(12) United States Patent
Lee

(10) Patent No.: US 10,040,772 B1
(45) Date of Patent: Aug. 7, 2018

(54) QUINOXALINE-FUSED DIBENZOSUBERANE BASED HELICENES AND ORGANIC ELECTROLUMINESCENT DEVICE USING THE SAME

(71) Applicant: JUST ABOUT SHOWING CO., LTD., New Taipei (TW)

(72) Inventor: Jen-Cherng Lee, New Taipei (TW)

(73) Assignee: JUST ABOUT SHOWING CO., LTD., New Taipei (TW)

( * ) Notice: Subject to any disclaimer, the term of this patent is extended or adjusted under 35 U.S.C. 154(b) by 0 days.

(21) Appl. No.: 15/692,820

(22) Filed: Aug. 31, 2017

(30) Foreign Application Priority Data

May 12, 2017 (TW) .............................. 106115857 A

(51) Int. Cl.
*C07D 241/38* (2006.01)
*C09K 11/06* (2006.01)
*H01L 51/50* (2006.01)
*H01L 51/00* (2006.01)

(52) U.S. Cl.
CPC ............ *C07D 241/38* (2013.01); *C09K 11/06* (2013.01); *H01L 51/0032* (2013.01); *H01L 51/5012* (2013.01); *C09K 2211/1044* (2013.01)

(58) Field of Classification Search
CPC .................................................. C07D 241/38
See application file for complete search history.

*Primary Examiner* — Brian E McDowell
(74) *Attorney, Agent, or Firm* — Muncy, Geissler, Olds & Lowe, P.C.

(57) ABSTRACT

A quinoxaline-fused dibenzosuberane based helicene is shown in formula (1),

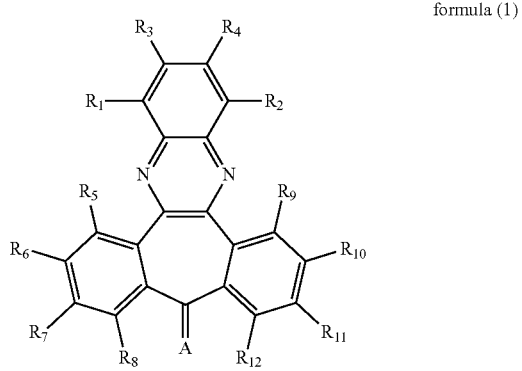

formula (1)

wherein A is with a structure of formula (2), formula (3a) or formula (3b);

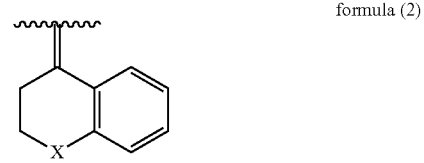

formula (2)

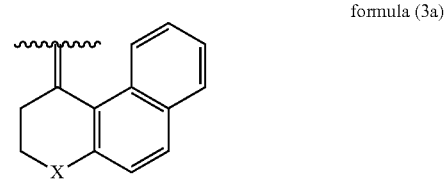

formula (3a)

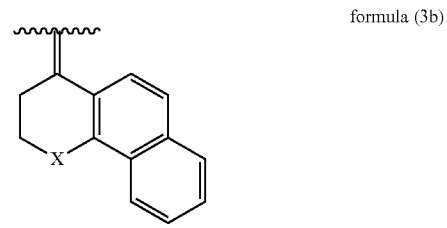

formula (3b)

X is an oxygen atom, sulfur atom, amino group, or $-(CH_2)_n-$, wherein n is 0, 1, or 2;
$R_1$ and $R_2$ are independently selected from the group consisting of hydrogen atom, halogen atom, formula (4), formula (5) and formula (6); and

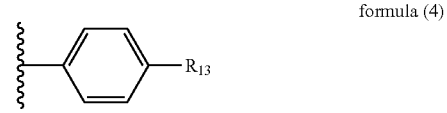

formula (4)

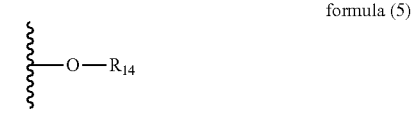

formula (5)

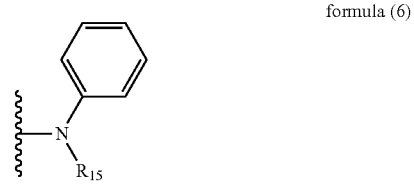

formula (6)

$R_3$ to $R_{15}$ are independently selected from the group consisting of hydrogen atom, halogen atom, cyano group, alkyl group, cycloalkyl group, alkoxy group, thioalkyl group, silyl group, alkenyl group, aryl group, heteroaryl group, and amino group.

10 Claims, 1 Drawing Sheet

QUINOXALINE-FUSED DIBENZOSUBERANE BASED HELICENES AND ORGANIC ELECTROLUMINESCENT DEVICE USING THE SAME

CROSS REFERENCE TO RELATED APPLICATIONS

This Non-provisional application claims priority under 35 U.S.C. § 119(a) on Patent Application No(s). 106115857 filed in Taiwan, Republic of China on May 12, 2017, the entire contents of which are hereby incorporated by reference.

BACKGROUND OF THE INVENTION

Field of Invention

The present invention relates to an organic electroluminescent material and an organic electroluminescent device using the same and, in particular, to a helicene derivative and the organic electroluminescent device using the same.

Related Art

With the advances in electronic technology, a light weight and high efficiency flat display device has been developed. An organic electroluminescent device becomes the mainstream of the next generation flat panel display device due to its advantages of self-luminosity, no restriction on viewing angle, power conservation, simple manufacturing process, low cost, high response speed, full color and so on.

In general, the organic electroluminescent device includes an anode, an organic luminescent layer and a cathode. When applying a direct current to the organic electroluminescent device, holes and electrons are injected into the organic luminescent layer from the anode and the cathode, respectively. Charge carriers move and then recombine in the organic luminescent layer because of the potential difference caused by an applied electric field. The excitons generated by the recombination of the electrons and the electron holes may excite the luminescent molecules in the organic luminescent layer. The excited luminescent molecules then release the energy in the form of light.

Moreover, the selection of organic electroluminescent material is not only based on the matching of HOMO and LUMO energy levels but also counts on the high decomposition temperature in order to avoid pyrolysis during thermal vacuum deposition and also thus avoid the decrease in thermal stability.

Accordingly, it is an urgent need to provide an organic electroluminescent material and an organic electroluminescent device using the same which have high luminous efficiency, and excellent thermal stability and film forming ability.

SUMMARY OF THE INVENTION

In view of the foregoing objectives, the invention provides a quinoxaline-fused dibenzosuberane based helicene and an organic electroluminescent device by using the same. The quinoxaline-fused dibenzosuberane based helicene has excellent luminous efficiency, thermal stability, and film forming ability.

To achieve the above objective, a quinoxaline-fused dibenzosuberane based helicene according to the present disclosure has a structure of the following General Formula (1).

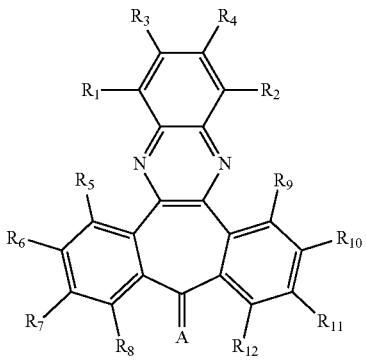

General Formula (1)

In General Formula (1), A is represented by General Formula (2), General Formula (3a) or General Formula (3b).

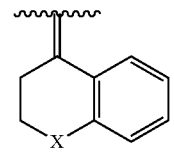

General Formula (2)

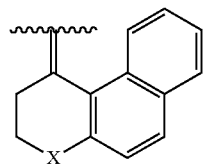

General Formula (3a)

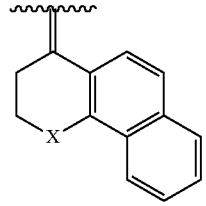

General Formula (3b)

In General Formula (1), X is an oxygen atom, sulfur atom, amino group, or $-(CH_2)_n$, n is 0, 1, or 2; $R_1$ and $R_2$ are both independently hydrogen atom, halogen atom, General Formula (4), General Formula (5) or General Formula (6),

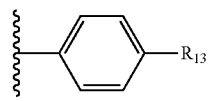

General Formula (4)

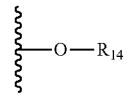

General Formula (5)

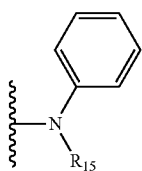

General Formula (6)

In General Formula (1), $R_3$ to $R_{15}$ are independently selected from the group consisting of hydrogen atom, halogen atom, cyano group, alkyl group, cycloalkyl group, alkoxy group, haloalkyl group, thioalkyl group, silyl group, alkenyl group, aryl group, and amino group.

To achieve the above objective, an organic electroluminescent device is also disclosed. The organic electroluminescent device comprises a first electrode layer, a second electrode layer and an organic luminescent unit. The organic luminescent unit is deposited between the first electrode layer and the second electrode layer. The organic luminescent unit has at least a quinoxaline-fused dibenzosuberane based helicene as shown in General Formula (1).

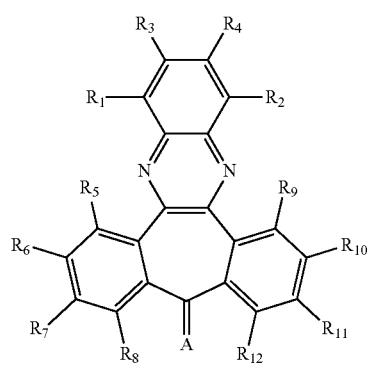

General Formula (1)

In General Formula (1), A is represented by General Formula (2), General Formula (3a) or General Formula (3b).

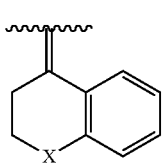

General Formula (2)

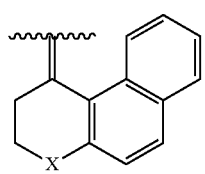

General Formula (3a)

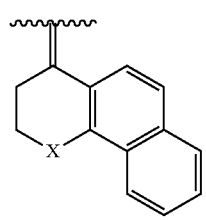

General Formula (3b)

In General Formula (1), X is an oxygen atom, sulfur atom, amino group, or $-(CH_2)_n-$, n is 0, 1, or 2; $R_1$ and $R_2$ are both independently hydrogen atom, halogen atom, General Formula (4), General Formula (5) or General Formula (6).

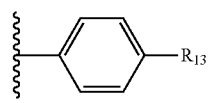

General Formula (4)

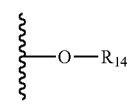

General Formula (5)

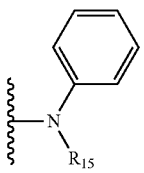

General Formula (6)

In General Formula (1), $R_3$ to $R_{15}$ are independently selected from the group consisting of hydrogen atom, halogen atom, cyano group, alkyl group, cycloalkyl group, alkoxy group, haloalkyl group, thioalkyl group, silyl group, alkenyl group, aryl group, and amino group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 3 to 6. The cycloalkyl group is a substituted or unsubstituted cycloalkyl group with the carbon number of 3 to 6. The alkoxy group is selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6. The silyl group is selected from the group consisting of a substituted or unsubstituted straight-chain silyl group with the carbon number of 1 to 6, and a substituted or unsubstituted branched-chain silyl group with the carbon number of 3 to 6. The alkenyl group is selected from the group consisting of a substituted or unsubstituted straight-chain alkenyl group with the carbon number of 2 to 6, and a substituted or unsubstituted branched-chain alkenyl group with the carbon number of 3 to 6. The aryl group is a substituted or unsubstituted aromatic hydrocarbon group with the carbon number of 6 to 16, or a substituted or unsubstituted hetero aromatic ring with the carbon number of 5 to 16. The amino group is a secondary amino group or a tertiary amino group.

In one embodiment, $R_{13}$ is an amino group or a substituted or unsubstituted straight-chain alkyl group with the carbon number of 1 to 6.

In one embodiment, $R_{14}$ is a substituted or unsubstituted straight-chain alkyl group with the carbon number of 1 to 6.

In one embodiment, $R_{15}$ is an aryl group or a substituted or unsubstituted straight-chain alkyl group with the carbon number of 1 to 6.

In one embodiment, the quinoxaline-fused dibenzosuberane based helicene is represented by one of following chemical formula I to chemical formula IV.

chemical formula I

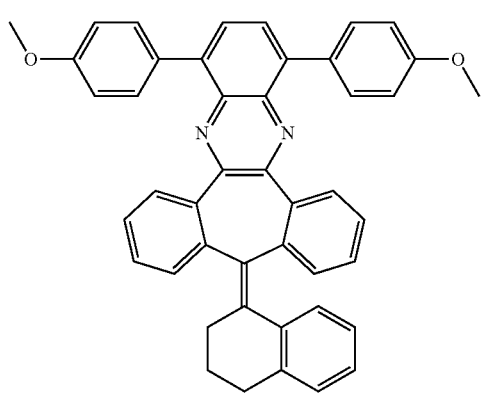

chemical formula II

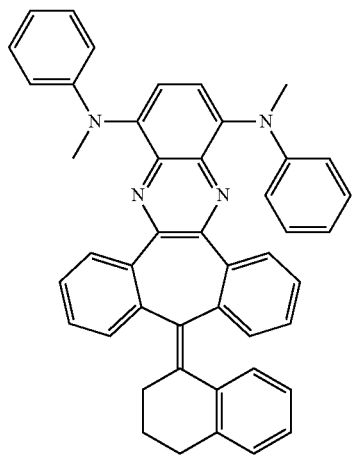

chemical formula III

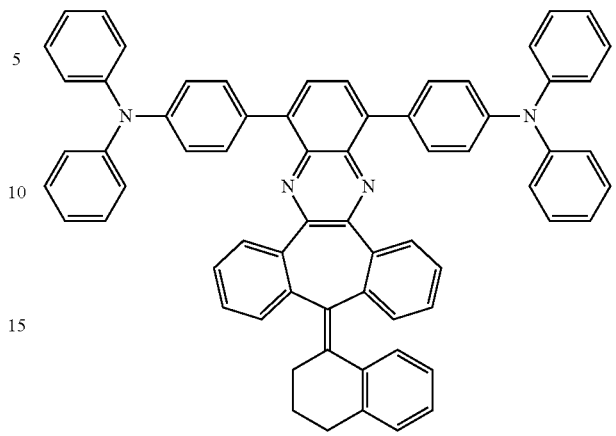

chemical formula IV

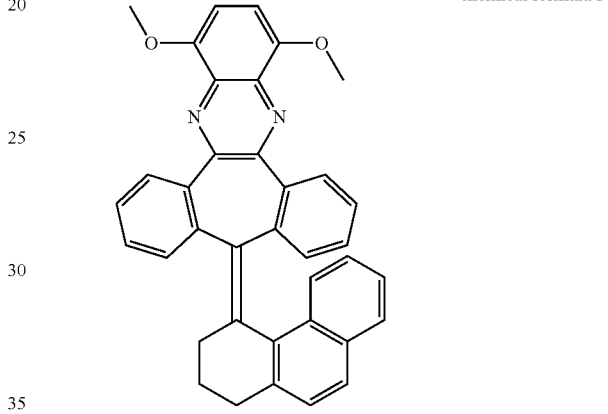

In one embodiment, the quinoxaline-fused dibenzosuberane based helicene has glass transition temperatures ranged from 108° C. to 146° C. and decomposition temperatures ranged from 385° C. to 547° C.

In one embodiment, the quinoxaline-fused dibenzosuberane based helicene has oxidation potentials ranged from 0.6V to 1.0V and redox potentials ranged from −1.60V to −1.66V.

In one embodiment, the quinoxaline-fused dibenzosuberane based helicene has highest occupied molecular orbital energy levels ($E_{HOMO}$) ranged from −5.28 eV to −5.98 eV and lowest unoccupied molecular orbital energy levels ($E_{LUMO}$) ranged from −3.14 eV to −3.20 eV.

In one embodiment, the organic luminescent unit comprises an organic luminescent layer.

In one embodiment, the organic luminescent unit further comprises a hole transport layer and an electron transport layer, and the organic luminescent layer is deposited between the hole transport layer and the electron transport layer.

In one embodiment, the organic luminescent unit further comprises a hole injection layer, a hole transport layer, an electron transport layer and an electron injection layer, and the hole transport layer, the organic luminescent layer and the electron transport layer are sequentially deposited between the hole injection layer and the electron injection layer.

In one embodiment, the organic luminescent layer comprises the quinoxaline-fused dibenzosuberane based helicene.

In one embodiment, the organic luminescent layer comprises a host material and a guest material, and the guest material comprises the quinoxaline-fused dibenzosuberane based helicene.

As mentioned above, the quinoxaline-fused dibenzosuberane based helicene according to some embodiments of the present invention has excellent fluorescence quantum effect and thermal stability. Therefore, the quinoxaline-fused dibenzosuberane based helicene is suitable for an organic electroluminescent device with excellent luminous efficiency and thermal stability.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

Figure 1:
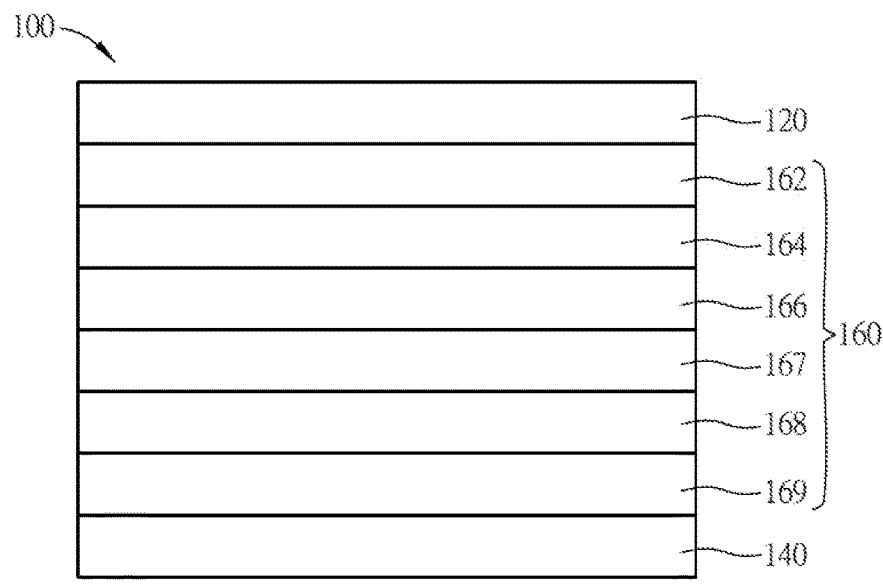
FIG. 1 is a cross-sectional schematic diagram of an organic electroluminescent device of the second embodiment according to the invention.

The embodiments of the invention will be apparent from the following detailed description, which proceeds with reference to the accompanying drawings, wherein the same references relate to the same elements.

Quinoxaline-Fused Dibenzosuberane Based Helicene

A quinoxaline-fused dibenzosuberane based helicene according to the first embodiment of the present invention has a structure of the following General Formula (1).

General Formula (1)

In General Formula (1), A is represented by General Formula (2), General Formula (3a) or General Formula (3b).

General Formula (2)

General Formula (3a)

General Formula (3b)

In General Formula (1), X is an oxygen atom, sulfur atom, amino group, or $-(CH_2)_n-$. n is 0, 1, or 2. $R_1$ and $R_2$ are each independently a hydrogen atom, a halogen atom, or a substituent with a structure represented by General Formula (4), General Formula (5) or General Formula (6).

General Formula (4)

General Formula (5)

General Formula (6)

In General Formula (1), $R_3$ to $R_{15}$ are independently selected from the group consisting of a hydrogen atom, halogen atom, cyano group, alkyl group, cycloalkyl group, alkoxy group, haloalkyl group, thioalkyl group, silyl group, alkenyl group, aryl group, and amino group.

In the present embodiment, the alkyl group is selected from the group consisting of a substituted or unsubstituted straight-chain alkyl group with the carbon number of 1 to 6, and a substituted or unsubstituted branched-chain alkyl group with the carbon number of 3 to 6. The cycloalkyl group is a substituted or unsubstituted cycloalkyl group with the carbon number of 3 to 6. The alkoxy group is selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6. The silyl group is selected from the group consisting of a substituted or unsubstituted straight-chain silyl group with the carbon number of 1 to 6, and a substituted or unsubstituted branched-chain silyl group with the carbon number of 3 to 6. The alkenyl group is selected from the group consisting of a substituted or unsubstituted straight-chain alkenyl group with the carbon number of 2 to 6, and a substituted or unsubstituted branched-chain alkenyl group with the carbon number of 3 to 6. The aryl group is a substituted or unsubstituted aromatic hydrocarbon group with the carbon number of 6 to 16, or a substituted or unsubstituted hetero aromatic ring with the carbon number of 5 to 16. The amino group is a secondary amino group or a tertiary amino group.

When the $R_1$ and $R_2$ in the quinoxaline-fused dibenzosuberane based helicene according to the first embodiment of the present invention are both represented by General formula (4), $R_{13}$ is an amino group or a substituted or unsubstituted straight-chain alkyl group with the carbon number of 1 to 6. On the other hand, when the $R_1$ and $R_2$ in the quinoxaline-fused dibenzosuberane based helicene according to the first embodiment of the present invention are both represented by General formula (5), $R_{14}$ is a substituted or unsubstituted straight-chain alkyl group with the carbon number of 1 to 6. When the $R_1$ and $R_2$ in the quinoxaline-fused dibenzosuberane based helicene according to the first embodiment of the present invention are both represented by General formula (6), $R_{15}$ is an aryl group or a substituted or unsubstituted straight-chain alkyl group with the carbon number of 1 to 6.

Accordingly, the quinoxaline-fused dibenzosuberane based helicenes in the present embodiment can be a series of compounds which are represented by the following General Formula (1-2-1) to General Formula (1-3b-5).

General Formula (1-2-1) to General Formula (1-2-5).

General Formula (1-2-1)

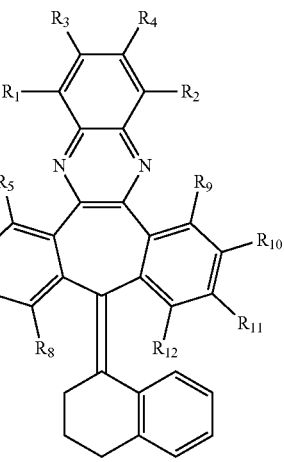

General Formula (1-2-2)

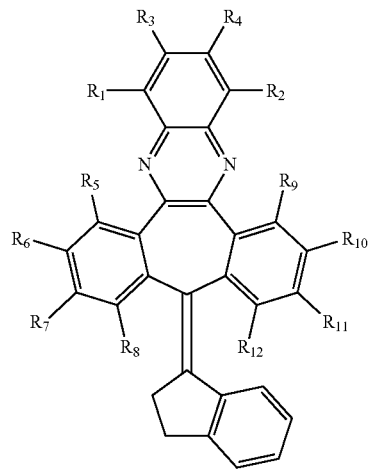

General Formula (1-2-3)

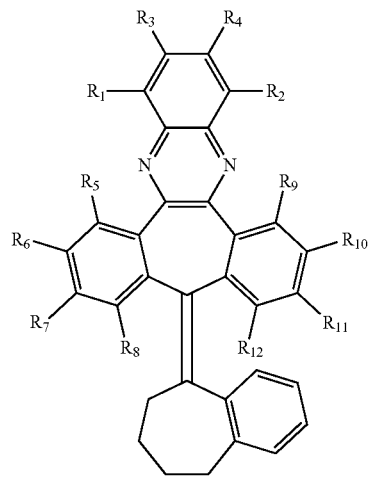

General Formula (1-2-4)

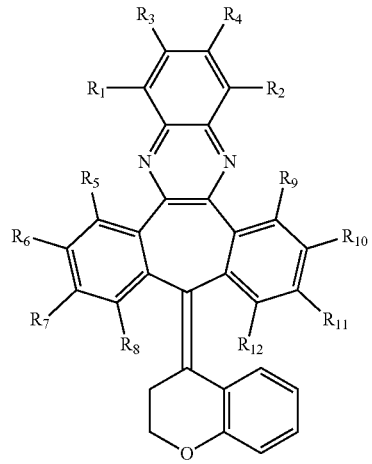

-continued
General Formula (1-2-5)
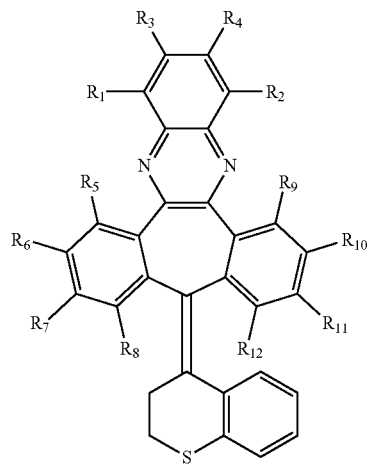
General Formula (1-3a-1) to General Formula (1-3a-5).
General Formula (1-3a-1)
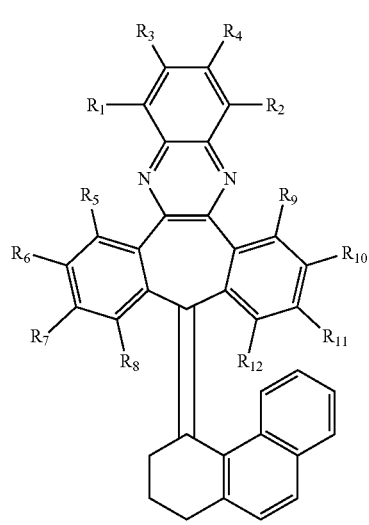
General Formula (1-3a-2)
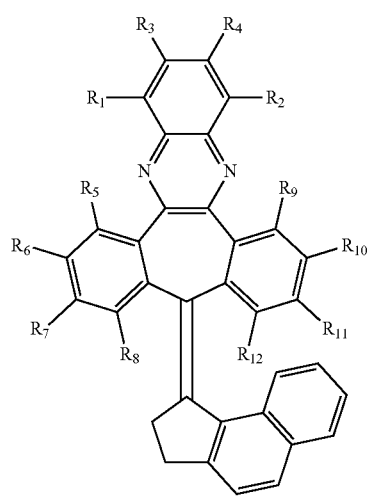
-continued
General Formula (1-3a-3)
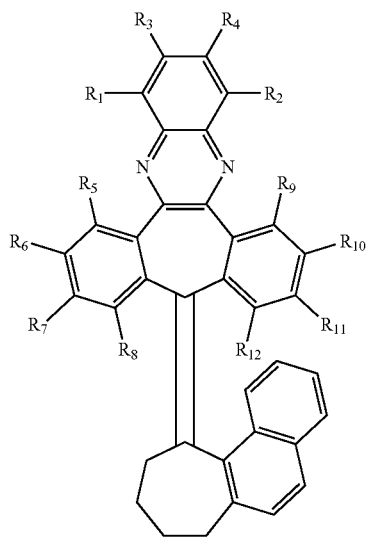
General Formula (1-3a-4)
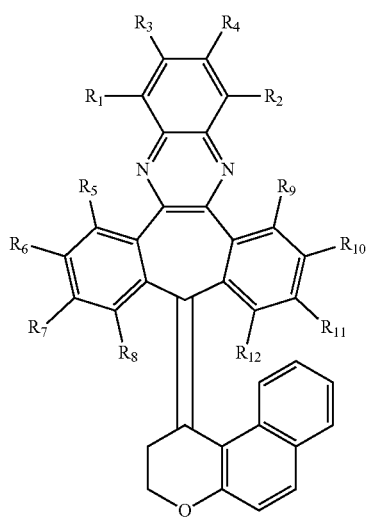
General Formula (1-3a-5)
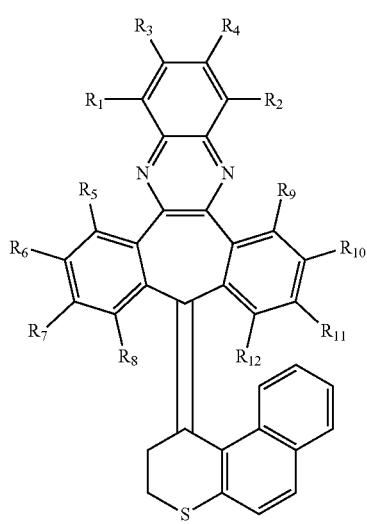

General Formula (1-3b-1) to General Formula (1-3b-5).

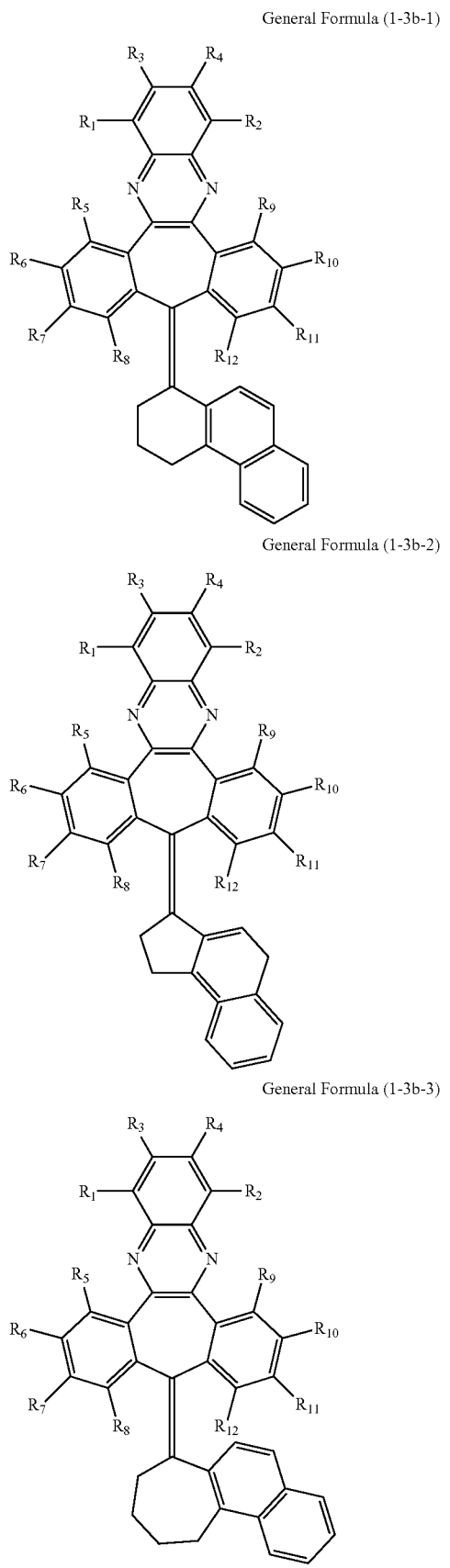

General Formula (1-3b-1)

General Formula (1-3b-2)

General Formula (1-3b-3)

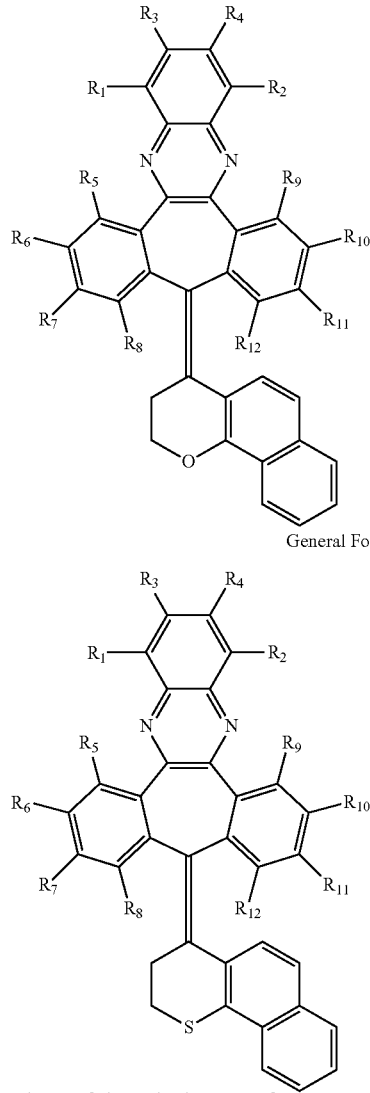

General Formula (1-3b-4)

General Formula (1-3b-5)

The selections of the substituents of $R_1$ to $R_{12}$ in General Formula (1-2-1) to General Formula (1-3b-5) are substantially the same as those in General Formula (1) and are therefore omitted here.

The quinoxaline-fused dibenzosuberane based helicene according to the present embodiment can be represented by following chemical formula I to chemical formula IV.

chemical formula I

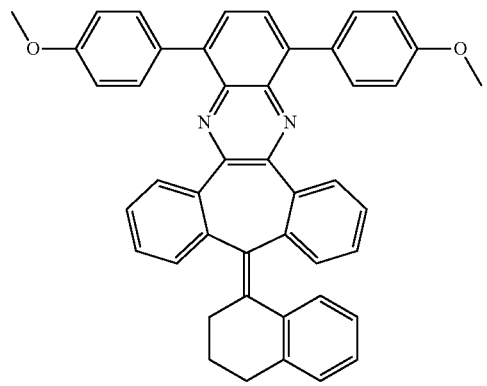

chemical formula II

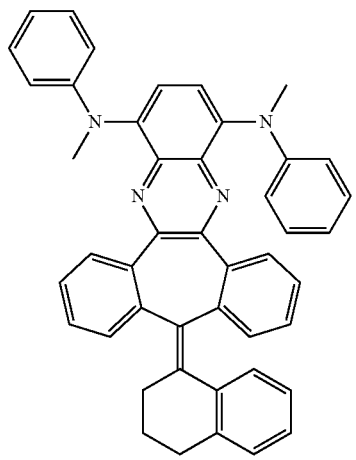

chemical formula III

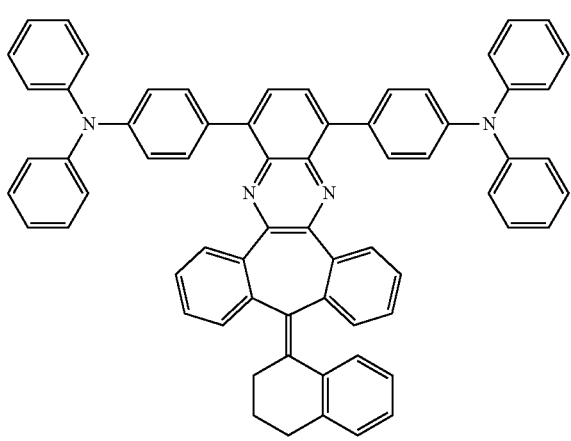

chemical formula IV

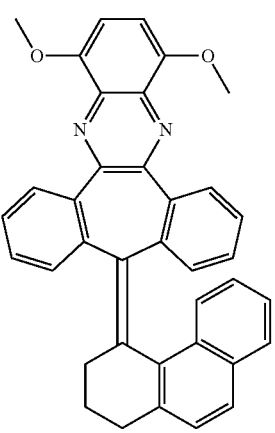

In the present embodiment, the quinoxaline-fused dibenzosuberane which is represented by General Formula (1) has a core template with a quinoxaline fragment as its upper panel and a helicene fragment (tetrahydronaphthalene or tetrahydro-phenanthrene) as its lower panel. Therefore, the resulting quinoxaline-fused dibenzosuberane based helicene compounds are suitable for an organic luminescent material, hole transport material, and/or electron transport material with high efficiency and excellent thermal stability.

In the present embodiment, the quinoxaline-fused dibenzosuberane based helicene materials have glass transition temperatures ranged from 108° C. to 146° C., decomposition temperatures ranged from 385° C. to 547° C., oxidation potentials ranged from 0.6V to 1.0V and redox potentials ranged from −1.60V to −1.66V. In addition, the highest occupied molecular orbital energy levels ($E_{HOMO}$) of the quinoxaline-fused dibenzosuberane based helicene materials are ranged from −5.28 eV to −5.98 eV and the lowest unoccupied molecular orbital energy levels ($E_{LUMO}$) of the quinoxaline-fused dibenzosuberane based helicene materials are ranged from −3.14 eV to −3.20 eV.

The thermal, optical, and electrochemical properties of the quinoxaline-fused dibenzosuberane based helicene according to the present embodiment are further illustrated in the following experimental examples.

Organic Electroluminescent Device

Please refer to FIG. 1, an organic electroluminescent device 100 of the second embodiment according to the disclosure includes a first electrode layer 120, a second electrode layer 140 and an organic luminescent unit 160. In the embodiment, the first electrode layer 120 can be a transparent electrode material, such as indium tin oxide (ITO), and the second electrode layer 140 can be a metal, transparent conductive substance or any other suitable conductive material. On the other hand, the first electrode layer 120 can also be a metal, transparent conductive substance or any other suitable conductive material, and the second electrode layer 140 can also be a transparent electrode material. Overall, at least one of the first electrode layer 120 and the second electrode layer 140 of the embodiment is a transparent electrode material, so that the light emitted from the organic luminescent unit 160 may pass through the transparent electrode, thereby enabling the organic electroluminescent device 100 to emit light.

In addition, please also refer to FIG. 1, the organic luminescent unit 160 can comprise a hole transport layer 162, an electron blocking layer 164, an organic luminescent layer 166, a hole blocking layer 167, an electron transport layer 168 and an electron injection layer 169. The electron blocking layer 164, the organic luminescent layer 166, the hole blocking layer 167 and the electron transport layer 168 are sequentially deposited between the hole transport layer 162 and the electron injection layer 169.

Herein, the materials of the hole transport layer 162 can be 1,1-Bis[4-[N,N′-di(p-tolyl)amino]phenyl]cyclohexane (TAPC), N,N-bis-(1-naphthyl)-N,N-diphenyl-1,1-biphenyl-4,4-diamine (NPB), N—N′-diphenyl-N—N′bis(3-methyl-phenyl)-[1-1′-biphenyl]-4-4′-diamine (TPD), or 4,4′,4″-tri (N-carbazolyl)triphenylamine (TCTA) and so on. Moreover, the thickness of the hole transport layer 162 of the embodiment is, for example, greater than 0 nm and no more than 40 nm. The materials of electron blocking layer 164 can be N,N′-dicarbazolyl-3,5-benzene (mCP) or other materials which have lower electron affinity. The materials of hole blocking layer 167 can be 2,9-Dimethyl-4,7-diphenyl-1,10-phenanthroline (BCP), or 9,10-bis(3-(pyridin-3-yl)phenyl) anthracene (DPyPA). Moreover, the thickness of the hole blocking layer 167 of the embodiment is, for example, greater than 0 nm and no more than 15 nm.

The materials of the electron transport layer 168 can be Tris-(8-hydroxyquinoline)aluminum ($Alq_3$), or 2,2,2-(1,3,5-benzinetriyl)-tris(1-phenyl-1-H-benzimidazole) (TBPI). In the embodiment, the thickness of the electron transport layer 168 is, for example, greater than 0 nm and no more than 45 nm. The electron transport layer 168 may further increase the transport rate of the electron from the electron injection layer 169 to the organic luminescent layer 166.

In addition, the thickness of the organic luminescent layer 166 of the embodiment is between 5 nm and 45 nm, for example, 15 nm or 40 nm. The quinoxaline-fused dibenzosuberane based helicene which has a structure of General Formula (1) can be a suitable material used in the organic luminescent layer 166, the hole transport layer 162, and/or the electron transport layer 168.

General Formula (1)

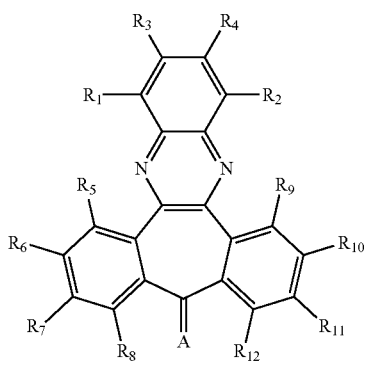

In General Formula (1), A is represented by General Formula (2), General Formula (3a) or General Formula (3b).

General Formula (2)

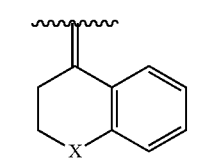

General Formula (3a)

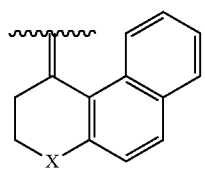

General Formula (3b)

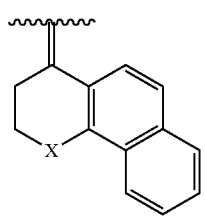

In General Formula (1), X is an oxygen atom, sulfur atom, amino group, or —(CH$_2$)$_n$. n is 0, 1, or 2. R$_1$ and R$_2$ are each independently a hydrogen atom, a halogen atom, or a substituent which can be represented by the following General Formula (4), General Formula (5) or General Formula (6).

General Formula (4)

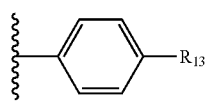

General Formula (5)

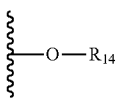

General Formula (6)

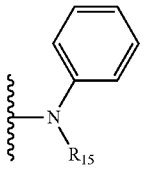

In addition, the various examples and the selection of the substituents of R$_1$ to R$_{15}$ of General Formula (1), as well as their properties, such as their decomposition temperatures (T$_d$), oxidation potentials, redox potentials, highest occupied molecular orbital energy levels (E$_{HOMO}$), and lowest unoccupied molecular orbital energy levels (E$_{LUMO}$), are substantially the same as those in the first embodiment and are therefore omitted here.

Figure 2:
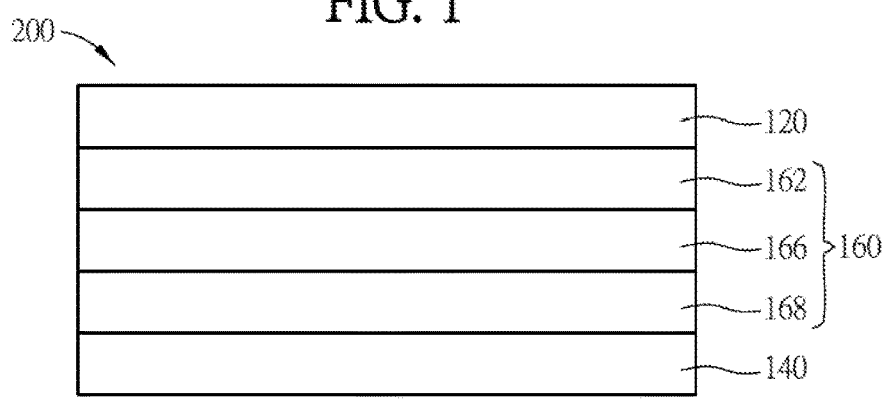
FIG. 2 is a cross-sectional schematic diagram of an organic electroluminescent device of the third embodiment according to the invention.

In addition, FIG. 2 is a cross-sectional schematic diagram of an organic electroluminescent device 200 of the third embodiment according to the invention. The configuration of the organic electroluminescent device 200 is substantially similar with that of the organic electroluminescent device 100, and same elements have substantial the same characteristics and functions. Therefore, the similar references relate to the similar elements, and detailed explanation is omitted hereinafter.

Please refer to FIG. 2, in the embodiment, the organic luminescent unit 160 can comprise a hole transport layer 162, an organic luminescent layer 166 and an electron transport layer 168. The organic luminescent layer 166 is deposited between the hole transport layer 162 and the electron transport layer 168.

Figure 3:
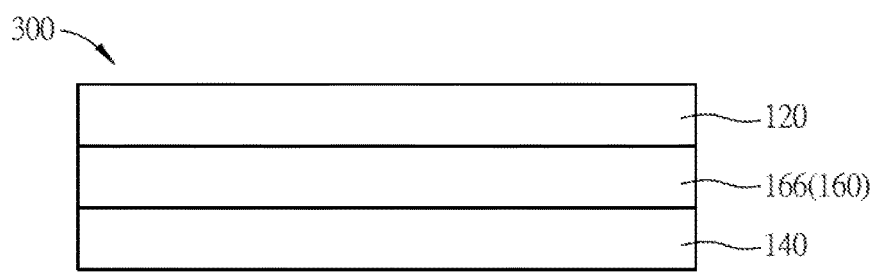
FIG. 3 is a cross-sectional schematic diagram of an organic electroluminescent device of the fourth embodiment according to the invention.

In addition, FIG. 3 is a cross-sectional schematic diagram of an organic electroluminescent device 300 of the fourth embodiment according to the invention. The configuration of the organic electroluminescent device 300 is substantially similar with that of the organic electroluminescent device 100, and same elements have substantial the same characteristics and functions. Therefore, the similar references relate to the similar elements, and detailed explanation is omitted hereinafter.

Please refer to FIG. 3, in the embodiment, the organic luminescent unit 160 can comprise an organic luminescent layer 166.

Moreover, the configuration of the organic electroluminescent device according to the invention is not limited to what is disclosed in the second, third or fourth embodiment. The second, third and fourth embodiments are embodiments for illustration.

To illustrate the synthesis of the compounds according to the embodiment, there are several examples shown below.

Example 1: Synthesis of Compound 1
(1,2,3,4-tetrahydro-1-naphthalenone hydrazone)

A two-necked 100 mL flask was installed on a Dean-Stark trap and then dried under vacuum. Ethanol (30 mL) was added to the 100 ml flask, followed by adding α-tetralone (400 μL, 3 mmol) and hydrazine monohydrate (2.62 mL, 54 mmol) into the flask by a syringe. The flask containing the reaction mixture was then put in an oil bath at 120° C. for being refluxed for 2 hours, and then the flask was removed from the heating system and cooled down to room temperature. The ethanol was removed by a vacuum system so as to obtain the product 1 (yield: 100%). Because the product 1 tended to decompose easily, it was used for the following reactions without purification. The above reaction is represented by the chemical equation (1-1).

Spectral data as follow: M.W.: 106.10; $^1$H NMR (400 MHz, CDCl$_3$) δ 8.32 (d, J=7.6, 1H), 7.21-7.16 (m, 2H), 7.11 (t, J=2.4, 1H), 5.32 (s, 1H), 2.73 (t, J=6.4, 2H), 2.47 (t, J=6.8, 2H), 1.92 (dd, J=6.4, 2.4, 2H).

chemical equation (1-1)

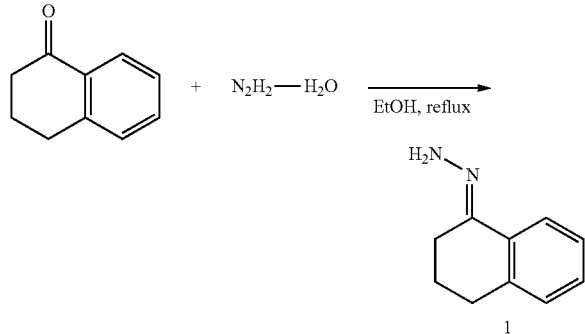

Example 2: Synthesis of Compound 2 (dibenzo[a,d]cycloheptene-5-thione)

P$_4$S$_{10}$ (2.68 g, 6.03 mmol) and anhydrous CH$_3$CN (10 mL) were added to a two-necked, round-bottomed 100 mL flask. Dibenzosuberenone (1.054 g, 5.11 mmol) dissolved by anhydrous CH$_3$CN (15 mL) was added into another two-necked, round-bottomed flask, and was injected to the first (100 ml) flask by a double-tipped needle. The mixture was then reacted for 2 days at room temperature, and the reaction was quenched by the following steps. The reaction mixture was first filtered by Al$_2$O$_3$ to removed P$_4$S$_{10}$ and P$_4$O$_{10}$. The green filtrate (liquid) was then condensed with a rotary evaporator to obtain a crude product. The crude product was then purified by column chromatography by using a mixture of EtOAc/hexanes (1/30) as an eluent, and followed by recrystallization with n-hexane, so as to obtain the green compound 2 (569 mg, yield: 50%). The above reaction is represented by the chemical equation (1-2).

Spectral data as follow: M.W.: 222.30; $^1$H NMR (400 MHz, CDCl$_3$) δ 8.03 (dd, J=7.8, 0.9, 2H), 7.50 (td, J=7.5, 1.2, 2H), 7.42-7.35 (m, 4H), 6.99 (s, 2H); $^{13}$C NMR (100 MHz, CDCl$_3$) δ 149.52, 136.48, 130.97, 129.54, 128.95, 126.28, 33.73; TLC R$_f$=0.43 (EtOAc/hexanes, 1/30); Elemental Analysis. Calcd for C$_{15}$H$_{12}$S: C, 80.32; H, 5.39; Found: C, 80.33; H, 5.42.

chemical equation (1-2)

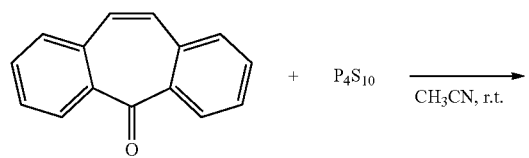

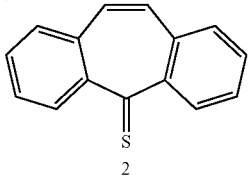

Example 3a: Synthesis of Compound 3a (1'H-thiochromane-1'-2"-thiirane-3"-10,11-dihydro-5H-dibenzo[a,d]cycloheptene)

Each end (top and bottom) of a Schlenk tube was installed with a two-necked 50 ml flask which was then dried by vacuum. The compound 1 (480.3 mg, 3 mmol) dissolved in anhydrous dichloromethane (10 mL) was transferred into the flask installed at the bottom end of the Schlenk tube by a double-tipped needle. At –10° C., dried silver(I) oxide (1.04 g, 4.5 mmol) and magnesium sulfate (1.95 g) were well mixed and then poured into the flask at bottom end of the Schlenk tube. Saturated potassium hydroxide solution (in methanol, 2.35 mL) was dropwisely injected into the flask at the bottom end of the Schlenk tube. After reacting for 40 minutes at –10° C., the Schlenk tube was inverted to filter out the solid impurities (i.e., silver(I) oxide and magnesium sulfate) and thus to collect the dark-red filtrate in the other two-necked flask. Then the flask containing the filtrate was placed at 0° C. The compound 2 (thioketone, 333.8 mg, 1.57 mmol) dissolved in anhydrous dichloromethane (15.7 mL, concentration: 0.1M) was then slowly injected into the flask containing the filtrate with an air-tight syringe until no bubbles were produced in the solution and the color of the solution became light green (the color of compound 2). After reacting for 9 hours at 0° C., the reaction mixture was added with saturated, aqueous sodium bicarbonate solution (10 mL) to quench the reaction. The organic layer of the reaction mixture was then extracted with dichloromethane (150 mL). The collected organic layer was dried by adding anhydrous magnesium sulfate, followed by filtration and condensation to obtain a crude product. The crude product was then purified by column chromatography by using a mixture of ether/hexane (1/100) as an eluent, and was then recrystallized with a mixture of hexanes/dichloromethane, so as to obtain the compound 3a (243 mg, yield: 69%). The above reaction is represented by the chemical equation (1-3a).

Spectral data as follow: M.W.: 352.49; mp 112-116° C.; $^1$H NMR: (400 MHz, CDCl$_3$) δ 7.85 (d, J=7.8, 1H), 7.69 (d, J=7.5, 1H), 7.33-7.19 (m, 4H), 7.08 (t, J=7.3, 1H), 6.92-6.89 (m, 2H), 6.83-6.78 (m, 2H), 6.48 (d, J=11.7, 1H), 6.40 (dt, J=8, 1.9, 1H), 6.35 (d, J=7.8, 1H), 2.70 (t, J=5.6, 2H), 1.93 (dt, J=11.5, 3.4, 1H), 1.87-1.80 (m, 1H), 1.56-1.48 (m, 1H), 1.36-1.30 (m, 1H); $^{13}$C NMR: (100 MHz, CDCl$_3$) δ 139.94, 139.85, 137.73, 135.61, 135.16, 134.81, 132.23, 131.50, 131.34, 130.08, 129.47, 129.13, 129.84, 128.70, 128.36, 127.57, 127.49, 127.18, 126.91, 124.39, 68.68, 56.91, 34.99, 29.22, 21.55; MS: (20 eV) 352 (M$^+$, 60), 351(31), 319 (12), 189 (100); Analysis: (C$_{25}$H$_{20}$S (352.49)) Calcd: C, 85.18; H, 5.72; S, 9.10; Found: C, 85.23; H, 5.79; TLC: R$_f$ 0.3 (hexane/ether, 100/1).

chemical equation (1-3a)

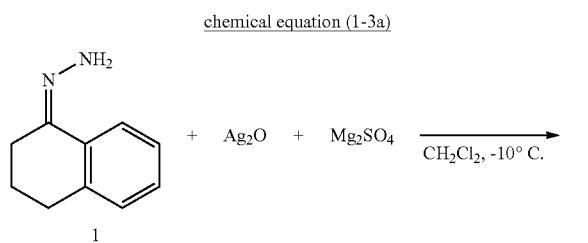

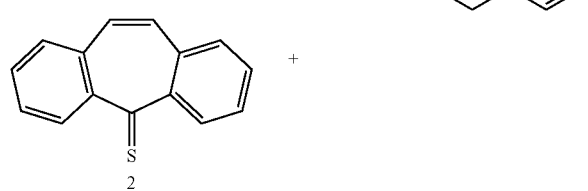

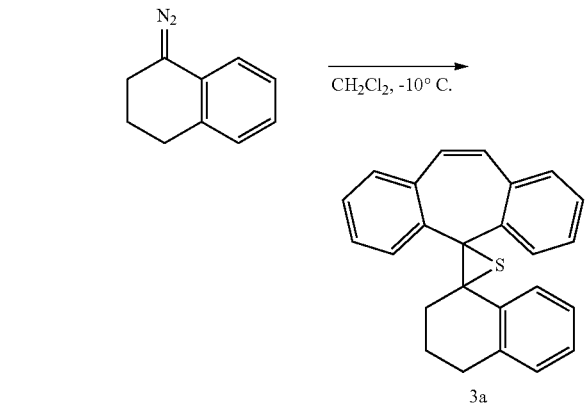

Example 3b: Synthesis of Compound 3b (2",3"-dihydrodispiro[dibenzo[a,d][7]annulene-5,2'-thiirane-3',1"-indene])

Each end (top and bottom) of a Schlenk tube was installed with a two-necked 100 ml flask which was then dried by vacuum. The compound 1b (488.5 mg, 3 mmol) dissolved in anhydrous dichloromethane (30 mL) was transferred into the flask installed at bottom end of the Schlenk tube by a double-tipped needle. At −10° C., dried silver(I) oxide (1.04 g, 4.5 mmol) and magnesium sulfate (1.96 g) were well mixed and then poured into the flask at bottom end of the Schlenk tube, followed by being dropwisely added with saturated potassium hydroxide solution (in methanol, 0.87 mL). After reacting for 40 minutes at −10° C., the Schlenk tube was inverted to filter out the solid impurities (i.e., silver(I) oxide and magnesium sulfate) and thus to collect the dark-red filtrate in the other two-necked flask. Then the flask containing the filtrate was placed at 0° C. The compound 2 (thioketone, 401.9 mg, 1.8 mmol) dissolved in anhydrous dichloromethane (18 mL) was then slowly injected into the flask containing the filtrate with an air-tight syringe until no bubbles were produced in the solution and the color of the solution became light green (the color of compound 2). After reacting for 10 hours at 0° C., the reaction mixture was added with saturated, aqueous sodium bicarbonate solution (10 mL) to quench the reaction. The organic layer of the reaction mixture was then extracted with dichloromethane (150 mL) for three times. Then, the collected organic layer was dried by adding anhydrous magnesium sulfate, followed by filtration and condensation to obtain a condensed solution. The condensed solution was then purified by column chromatography by using n-hexane as an eluent to obtain a crude product. The crude product was then recrystallized with n-hexane, so as to obtain the compound 3b (222.9 mg, yield: 37%). The above reaction is represented by the chemical equation (1-3b).

Spectral data as follow: m.p.: 138-141° C.; $^1$H NMR: (400 MHz, CDCl$_3$) 7.85 (d, J=8.0, 1H), 7.70 (d, J=8.0, 1H), 7.73 (dt, J=8.0, 4.0, 2H), 7.28-7.21 (m, 2H), 7.19 (t, J=8.0, 1H), 7.05-6.98 (m, 3H), 6.89 (d, J=12.0, 1H), 6.63 (t, J=8.0, 1H), 6.42 (d, J=12, 1H), 5.76 (d, J=8.0, 1H), 2.94-2.81 (m, 2H), 2.24-2.16 (m, 1H), 1.70-1.64 (m, 1H); $^{13}$C NMR: (100 MHz, CDCl$_3$) 145.18, 145.18, 142.96, 140.72, 138.92, 135.63, 135.18, 132.1, 131.17, 130.58, 129.75, 128.72, 127.96, 127.63, 127.36, 126.05, 124.85, 124.1, 64.92, 63.59, 34.55, 29.57; MS: (20 eV) 338 (M$^+$, 100), 337 (20), 189 (94), 115 (10), 91 (28); TLC: R$_f$0.37 (hexane).

chemical equation (1-3b)

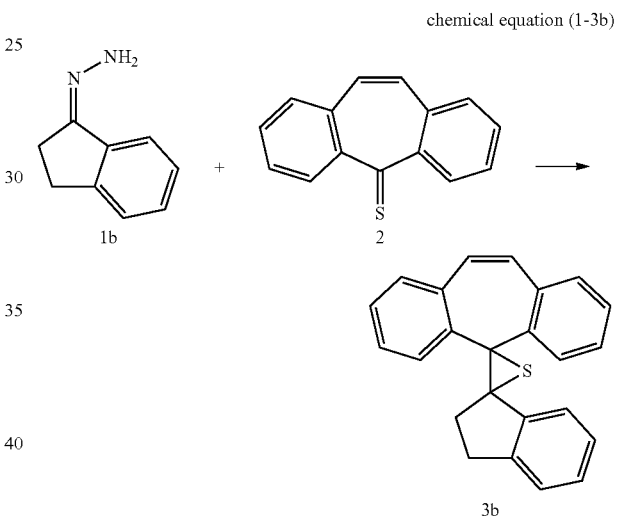

Example 3c: Synthesis of Compound 3c (6,7,8,9-tetrahydrodispiro[benzo[7]annulene-5,2'-thiirane-3',5"-dibenzo[a,d][7]annulene])

Each end (top and bottom) of a Schlenk tube was installed with a two-necked 100 ml flask which was then dried by vacuum. The compound 1c (522.7 mg, 3 mmol) dissolved in anhydrous dichloromethane (25 mL) was then transferred into the flask installed at bottom end of the Schlenk tube by a double-tipped needle. At −10° C., dried silver(I) oxide (1.04 g, 4.5 mmol) and magnesium sulfate (1.96 g) were well mixed and then poured into the flask at bottom end of the Schlenk tube, followed by dropwisely addition of saturated potassium hydroxide solution (in methanol, 2.4 mL) into the flask at bottom end of the Schlenk tube. After reacting for 40 minutes at −10° C., the Schlenk tube was inverted to filter out the solid impurities (i.e., silver oxide and magnesium sulfate) and thus to collect the dark-red filtrate in the other two-necked flask. Then the flask containing the filtrate was placed at 0° C. The compound 2 (thioketone, 552 mg, 2.48 mmol) dissolved in anhydrous dichloromethane (24.5 mL) was slowly injected into the flask containing the filtrate with an air-tight syringe until no bubbles were produced in the solution and the color of the solution became light green (the color of compound 2). After reacting for 4 hours at 0° C., the reaction mixture was added with saturated, aqueous sodium bicarbonate solution (5 mL) to quench the reaction. The organic layer of the reaction mixture was then extracted with ether (200 mL) for three times. Then, the collected organic layer was dried by adding anhydrous magnesium sulfate, followed by filtration and condensation to obtain a condensed solution. The condensed solution was then purified by column chromatography using a mixture of ether/n-hexane (1/100) as an eluent, so as to obtain a crude product. The crude product was recrystallized with n-hexane to obtain the compound 3c (654 mg, yield: 73%). The above reaction is represented by the chemical equation (1-3c).

Spectral data as follow: m.p.: 137-140° C.; $^1$H NMR: (200 MHz, CDCl$_3$) 7.79-7.72 (m, 2H), 7.42-6.84 (m, 10H), 6.78 (d, J=12.0, 1H), 6.64-6.55 (m, 1H), 3.3-3.21 (m, 1H), 2.63 (dt, 1H, J=14.0, 4.0), 2.05-1.96 (m, 1H), 1.66-1.45 (m, 5H); $^{13}$C NMR: (50 MHz, CDCl$_3$) 141.40, 139.32, 137.65, 137.12, 134.79, 134.54, 132.59, 132.59, 131.25, 130.98, 130.61, 129.92, 129.82, 128.46, 128.02, 127.56, 126.94, 126.94, 126.47, 124.7, 69.49, 65.33, 37.99, 33.50, 26.55, 23.16; MS: (20 eV) 366 (M$^+$, 100), 333 (11), 191 (35); TLC: R$_f$ 0.47 (hexane/ether, 100/1).

filtrate in the other two-necked flask. Then the flask containing the filtrate was placed at 0° C. The compound 2 (thioketone, 552 mg, 2.48 mmol) dissolved in anhydrous dichloromethane (24.5 mL) was slowly injected into the flask containing the filtrate with an air-tight syringe until no bubbles were produced in the solution and the color of the solution became light green (the color of compound 2). After reacting for 4 hours at 0° C., the reaction mixture was added with saturated, aqueous sodium bicarbonate solution (5 mL) to quench the reaction. The organic layer of the reaction mixture was then extracted with ether (200 mL) for three times. Then, the collected organic layer was dried by adding anhydrous magnesium sulfate, followed by filtration and condensation to obtain a condensed solution. The condensed solution was then purified by column chromatography by using a mixture of ether/n-hexane (1/100) as an eluent, so as to obtain a crude product. The crude product was recrystallized with n-hexane to obtain the compound 3d (106 mg, yield: 30%). The above reaction is represented by the chemical equation (1-3d).

Spectral data as follow: m.p.: 208-211° C.; $^1$H NMR: (200 MHz, CDCl$_3$) 7.92 (d, J=8, 1H), 7.73 (d, J=8.0, 1H), 7.44-7.28 (m, 5H), 7.26-7.14 (m, 3H), 7.07-6.72 (m, 2H), 6.66-6.61 (m, 2H), 6.27-6.24 (m, 2H), 4.25 (td, J=11.0, 3.0, 1H), 4.10-4.00 (m, 1H), 2.27 (td, J=12.0, 4.0, 1H), 1.42 (dt, J=12.0, 3.0, 1H); $^{13}$C NMR: (50 MHz, CDCl$_3$) 156.41, 136.44, 134.92, 134.1, 131.48, 131.43, 130.81, 130.81, 129.7, 129.23, 128.78, 128.41, 128.31, 127.93, 127.32, 127.23, 126.99, 120.65, 118.7, 116.19, 67.78, 65.31, 52.43, 33.09; MS: (20 eV) 354 (M$^+$, 100), 326 (83), 321 (72), 311 (44), 293 (25), 247 (88), 221 (44), 189 (100), 178 (21), 131 (48); TLC: R$_f$ 0.48 (hexane/ether, 1/20).

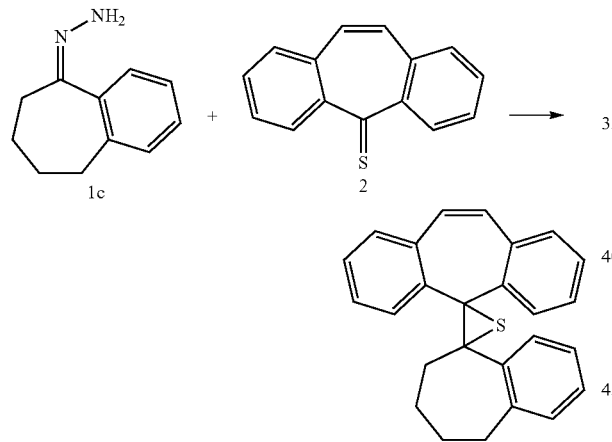

chemical equation (1-3c)

Example 3d: Synthesis of Compound 3d (dispiro [chromane-4,2'-thiirane-3',5''-dibenzo[a,d][7]annulene])

Each end (top and bottom) of a Schlenk tube was installed with a two-necked 100 ml flask which was then dried by vacuum. The compound 1d (454.1 mg, 3 mmol) dissolved in anhydrous dichloromethane (25 mL) was then transferred into the flask installed at bottom end of the Schlenk tube by a double-tipped needle. At −10° C., dried silver(I) oxide (1.04 g, 4.5 mmol) and magnesium sulfate (1.96 g) were well mixed and then poured into the flask at bottom end of the Schlenk tube, followed by dropwisely addition of saturated potassium hydroxide solution (in methanol, 2.4 mL) into the flask at bottom end of the Schlenk tube. After reacting for 40 minutes at −10° C., the Schlenk tube was inverted to filter out the solid impurities (i.e., silver oxide and magnesium sulfate) and thus to collect the dark-red

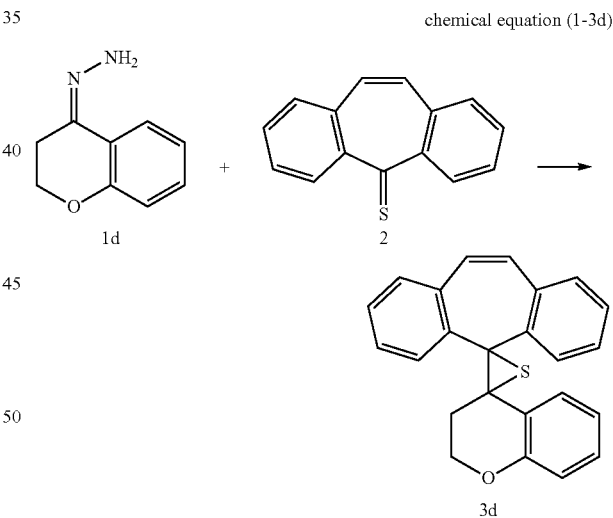

chemical equation (1-3d)

Example 3e: Synthesis of Compound 3e (dispiro [dibenzo[a,d][7]annulene-5,2'-thiirane-3',4''-thio-chromane])

Each end (top and bottom) of a Schlenk tube was installed with a two-necked 100 ml flask which was then dried by vacuum. The compound 1e (5344.1 mg, 3 mmol) dissolved in anhydrous dichloromethane (30 mL) was then transferred into the flask installed at bottom end of the Schlenk tube by a double-tipped needle. At −10° C., dried silver(I) oxide (1.04 g, 4.5 mmol) and magnesium sulfate (1.96 g) were well mixed and then poured into the flask at bottom end of the Schlenk tube, followed by dropwisely addition of saturated potassium hydroxide solution (in methanol, 2.4 mL) into the flask at bottom end of the Schlenk tube. After reacting for 40 minutes at −10° C., the Schlenk tube was inverted to filter out the solid impurities (i.e., silver oxide and magnesium sulfate) and thus to collect the dark-red filtrate in the other two-necked flask. Then the flask containing the filtrate was placed at 0° C. The compound 2 (thioketone, 333.4 mg, 1.5 mmol) dissolved in anhydrous dichloromethane (15 mL) was slowly injected into the flask containing the filtrate with an air-tight syringe until no bubbles were produced in the solution and the color of the solution became light green (the color of compound 2). After reacting for 4 hours at 0° C., the reaction mixture was added with saturated, aqueous sodium bicarbonate solution (10 mL) to quench the reaction. The organic layer of the reaction mixture was then extracted with ether (150 mL) for three times. Then, the collected organic layer was dried by adding anhydrous magnesium sulfate, followed by filtration and condensation to obtain a condensed solution. The condensed solution was then purified by column chromatography by using a mixture of ether/n-hexane (1/100) as an eluent, so as to obtain a crude product. The crude product was recrystalized with n-hexane to obtain the compound 3e (444 mg, yield: 80%). The above reaction is represented by the chemical equation (1-3e).

Spectral data as follow: m.p.: 191-192° C.; $^1$H NMR: (400 MHz, CDCl$_3$) 7.84 (d, J=8, 1H), 7.75 (d, J=8.0, 1H), 7.39-7.27 (m, 4H), 7.10 (td, J=8.0, 2.0, 1H), 7.02 (d, J=12.0, 1H), 6.94 (d, J=8.0, 1H), 6.89 (dd, J=8.0, 2.0, 1H), 6.79 (td, J=8.0, 4.0, 1H), 6.71-6.68 (m, 2H), 6.36 (td, J=8.0, 2.0, 1H), 3.14 (td, J=12.0, 4.0, 1H), 2.54 (dt, J=12.0, 4.0, 1H), 2.46 (td, J=16.0, 4.0, 1H), 1.64 (dt, J=16.0, 4.0, 1H); $^{13}$C NMR: (100 MHz, CDCl$_3$) 138.01, 138.01, 136.99, 135.76, 135.56, 135.00, 131.71, 131.6, 131.07, 130.81, 130.41, 129.21, 128.57, 128.39, 127.91, 127.62, 127.50, 127.36, 126.05, 122.57, 69.31, 55.93, 32.79, 24.64; MS: (20 eV) 370 (M$^+$, 100), 342 (70), 190 (22); TLC: R$_f$ 0.24 (hexane/ether, 100/1).

being dried under vacuum. The compound 3a (244.8 mg, 0.72 mmol) dissolved in anhydrous dimethylbenzene (2 mL) was added into the 10 ml flask, followed by adding dried copper powder (457.5 mg, 7.2 mmol). The 10 ml flask containing the reaction mixture was then put in an oil bath at 150° C. for reflux. The reaction mixture was refluxed for 2 hours, and then the red-brown copper powder was found to become black copper sulfide. After the reaction was completed, a crude product was collected with a filtering funnel which was fitted inside with a filter paper. The flask was washed by dichloromethane to collect the residual crude product in the flask. After filtration and condensation with a rotary evaporator, a white solid was obtained. The obtained solid was then recrystallized with a mixture of n-hexane/dichloromethane to obtain the compound 4a (207 mg, yield: 90%). The above reaction is represented by the chemical equation (1-4a).

Spectral data as follow: M.W.: 320.42; m.p.: 174-176° C.; $^1$H NMR (400 MHz, CDCl$_3$) δ 7.38-7.35 (m, 4H), 7.28-7.27 (m, 1H), 7.20 (t, J=7.4, 1H), 7.12-7.11 (m, 1H), 7.05-7.04 (m, 1H), 6.97 (dd, J=7.6, 2.5, 4H), 6.66 (t, J=7.5, 1H), 6.27 (d, J=7.9, 1H), 2.96-2.81 (m, 3H), 2.05-2.01 (m, 2H), 1.90-1.84 (m, 1H); $^{13}$C NMR (100 MHz, CDCl$_3$) δ 139.23, 139.20, 135.28, 135.20, 135.05, 131.36, 131.19, 129.29, 128.60, 128.58, 128.18, 128.14, 127.99, 127.58, 126.50, 126.36, 126.28, 124.22, 29.57, 28.16, 23.99; Elemental Analysis. Calcd for C$_{25}$H$_{22}$: C, 93.12; H, 6.88; Found: C, 92.88; H, 6.84; TLC: R$_f$ 0.30 (hexane/ether, 100/1); UV λ$_{max}$: 277 nm (ε 10060, in hexane).

chemical equation (1-3e)

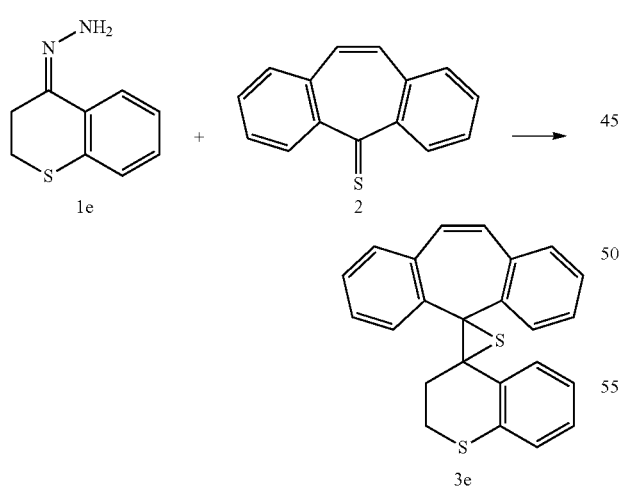

chemical equation (1-4a)

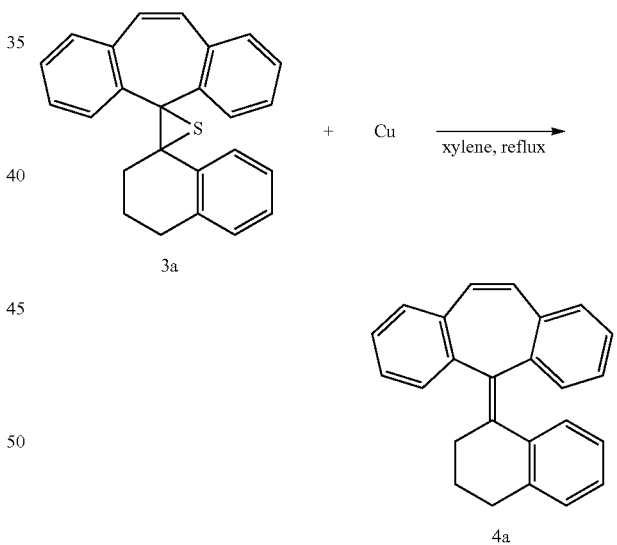

Example 4a: Synthesis of Compound 4a (5-(3,4-dihydro-2H-naphthalen-1-ylidene)-5H-dibenzo[a,d]cycloheptene)

A stir bar was placed in a 10 mL, two-necked flask, and the flask was then equipped to a condenser, followed by Example 4b: Synthesis of Compound 4b (5-(2,3-dihydro-1H-inden-1-ylidene)-5H-dibenzo[a,d][7]annulene)

A stir bar was placed in a 50 mL, two-necked flask, and the flask was then equipped to a condenser, followed by being dried under vacuum. The compound 3b (55.5 mg, 0.13 mmol) dissolved in anhydrous dimethylbenzene (10 mL) was added into the 50 ml flask, followed by adding dried copper powder (88.2 mg, 7.2 mmol). The 50 ml flask containing the reaction mixture was then put in an oil bath at 180° C. for reflux. The reaction mixture was refluxed for 2 hours, and then the red-brown copper powder was found to become black copper sulfide. After the reaction was completed, a crude product was collected with a filtering funnel which was fitted inside with a filter paper. The flask was washed by ether to collect the residual crude product in the flask. After filtration and condensation with a rotary evaporator, a white solid was obtained. The obtained solid was then purified by column chromatography by using n-hexane as an eluent, and followed by being recrystallized with n-hexane to obtain the compound 4b (36.2 mg, yield: 91%). The above reaction is represented by the chemical equation (1-4b).

Spectral data as follow: M.W.: 306.41; m.p.: 162-163° C.; $^1$H NMR (400 MHz, CDCl$_3$) δ 7.61-7.00 (m, 8H), 6.94 (s, 2H), 6.88-6.80 (m, 2H), 6.43 (d, J=8.0, 1H), 3.16-2.75 (m, 3H), 2.38-2.21 (m, 1H); $^{13}$C NMR (100 MHz, CDCl$_3$) δ 148.23, 148.22, 140.90, 140.45, 140.17, 138.90, 1334.42, 134.12, 131.08, 131.04, 128.70, 128.63, 128.55, 128.35, 128.1, 127.76, 127.55, 127.00, 126.30, 125.93, 125.14, 30.34, 29.60; MS (20 eV) 306 (M$^+$, 100); Elemental Analysis. Calcd for C$_{24}$H$_{18}$: C, 94.07; H, 5.93; Found: C, 94.02; H, 5.96; TLC: R$_f$ 0.34 (hexane/ether, 100/1); UV λ$_{max}$: 278 nm (ε 21200, in hexane).

was washed by ether to collect the residual crude product in the flask. After filtration and condensation with a rotary evaporator, a white solid of the compound 4c (84.4 mg, yield: 93%) was obtained. The above reaction is represented by the chemical equation (1-4c).

Spectral data as follow: M.W.: 334.45; m.p.: 152-153° C.; $^1$H NMR (200 MHz, CDCl$_3$) δ 7.57-7.52 (m, 1H), 7.42-7.21 (m, 6H), 7.07-6.88 (m, 8H), 6.71 (t, J=7.8, 2H), 6.44-6.26 (bd, J=8.0, 1H), 3.09 (t, J=12.0, 1H), 2.82 (t, J=12.0, 1H), 5.54-2.40 (bd, 1H), 2.04-1.87 (m, 4H), 1.60-1.40 (m, 1H); $^{13}$C NMR (100 MHz, CDCl$_3$) δ 142.99, 142.98, 142.92, 141.58, 138.90, 137.52, 134.70, 134.69, 131.19, 131.13, 129.86, 128.61, 128.29, 128.28, 128.01, 127.79, 127.78, 127.55, 126.58, 126.2, 125.96, 125.25, 36.64, 32.89, 32.37, 28.11; MS (20 eV) 334 (M$^+$, 100), 305 (11), 193 (12), 191 (80), 177 (11); Elemental Analysis. Calcd for C$_{26}$H$_{22}$: C, 93.37; H, 6.63; Found: C, 93.44; H, 6.82; TLC: R$_f$ 0.47 (hexane/ether, 100/1); UV λ$_{max}$: 251 nm (ε 12300, in hexane).

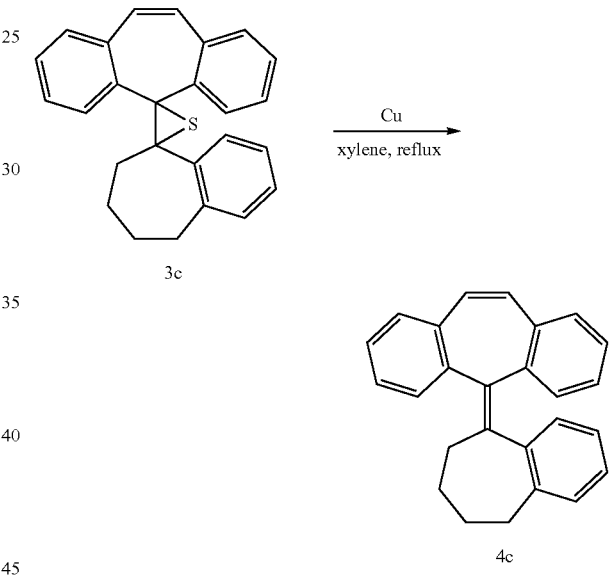

chemical equation (1-4c)

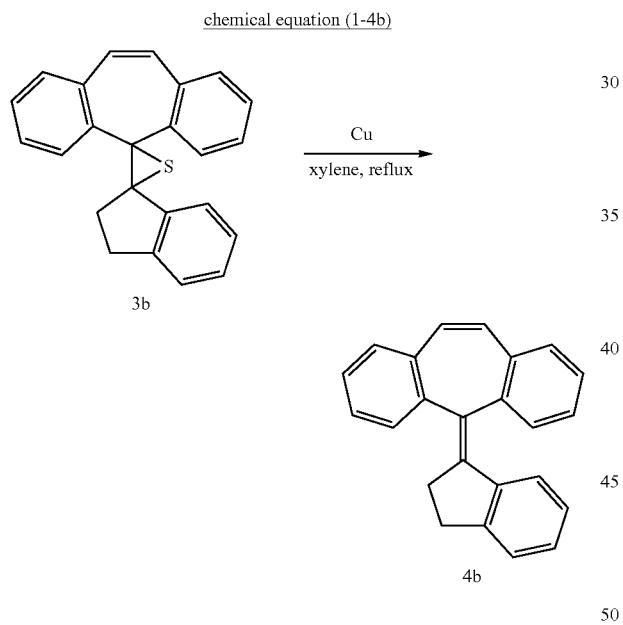

chemical equation (1-4b)

Example 4c: Synthesis of Compound 4c (5-(6,7,8, 9-tetrahydro-5H-benzo[7]annulen-5-ylidene)-5H-dibenzo[a,d][7]annulene)

A stir bar was placed in a 50 mL, two-necked flask, and the flask was then equipped to a condenser, followed by being dried under vacuum. The compound 3c (100 mg, 0.27 mmol) dissolved in anhydrous dimethylbenzene (10 mL) was added into the 50 ml flask, followed by adding dried copper powder (176.8 mg, 2.72 mmol). The 50 ml flask containing the reaction mixture was then put in an oil bath at 180° C. for reflux. The reaction mixture was refluxed for 2 hours, and then the red-brown copper powder was found to become black copper sulfide. After the reaction was completed, a crude product was collected with a filtering funnel which was fitted inside with a filter paper. The flask Example 4d: Synthesis of Compound 4d (4-(5H-dibenzo[a,d][7]annulen-5-ylidene)chromane)

A stir bar was placed in a 50 mL, two-necked flask, and the flask was then equipped to a condenser, followed by being dried under vacuum. The compound 3d (57.3 mg, 0.16 mmol) dissolved in anhydrous dimethylbenzene (10 mL) was added into the 50 ml flask, followed by adding dried copper powder (102.4 mg, 1.6 mmol). The 50 ml flask containing the reaction mixture was then put in an oil bath at 180° C. for reflux. The reaction mixture was refluxed for 2 hours, and then the red-brown copper powder was found to become black copper sulfide. After the reaction was completed, a crude product was collected with a filtering funnel which was fitted inside with a filter paper. The flask was washed by ether to collect the residual crude product in the flask. After filtration and condensation with a rotary evaporator, a white solid was obtained. The obtained solid was then purified by column chromatography by using a mixture of ether/n-hexane (1/100) as an eluent, and followed by being recrystallized with n-hexane to obtain the compound 4d (47.8 mg, yield: 93%). The above reaction is represented by the chemical equation (1-4d).

Spectral data as follow: M.W.: 322.40; m.p.: 226-227° C.; $^1$H NMR (400 MHz, CDCl$_3$) δ 7.35-7.13 (m, 8H), 7.00-6.86 (m, 3H), 6.69 (m, 1H), 6.31 (t, J=8.0, 1H), 6.10 (d, J=8.0, 1H), 4.49-4.46 (m, 1H), 4.34 (t, J=12.0, 1H), 2.83 (d, J=3.0, 1H), 2.18 (dt, J=12.0, 3.0, 1H); $^{13}$C NMR (100 MHz, CDCl$_3$) δ 156.15, 140.20, 139.06, 135.90, 135.59, 134.50, 134.49, 131.84, 130.00, 129.93, 129.61, 129.35, 129.25, 129.02, 128.92, 128.70, 127.72, 127.42, 127.15, 122.85, 119.42, 117.07, 67.71, 26.77; MS (20 eV) 322 (M$^+$, 100); Elemental Analysis. Calcd for C$_{24}$H$_{18}$O: C, 89.40; H, 5.63; Found: C, 89.45; H, 5.55; TLC: R$_f$ 0.37 (hexane/ether, 20/1); UV λ$_{max}$: 272 nm (ε 7553, in hexane).

Spectral data as follow: M.W.: 338.47; m.p.: 242-243° C.; $^1$H NMR (400 MHz, CDCl$_3$) δ 7.43-6.89 (m, 12H), 6.55 (td, J=7.0, 1.0, 1H), 6.24 (dd, J=7.0, 1.4, 1H), 3.48-3.20 (m, 2H), 3.02 (dt, J=12.0, 4.0, 1H), 2.10 (td, J=12.0, 5.0, 1H); $^{13}$C NMR (100 MHz, CDCl$_3$) δ 140.47, 140.46, 138.90, 137.36, 136.52, 135.79, 135.70, 134.55, 131.90, 131.88, 130.79, 129.64, 129.21, 128.98, 128.70, 128.66, 127.71, 127.38, 127.32, 127.24, 126.87, 123.49, 28.49, 26.83; MS (20 eV) 339 (24), 338 (M$^+$, 100), 323 (24), 191 (17); Elemental Analysis. Calcd for C$_{24}$H$_{18}$S: C, 85.17; H, 5.36; Found: C, 84.86; H, 5.39; TLC: R$_f$ 0.34 (hexane/ether, 100/1); UV λ$_{max}$: 279 nm (ε 26800, in hexane).

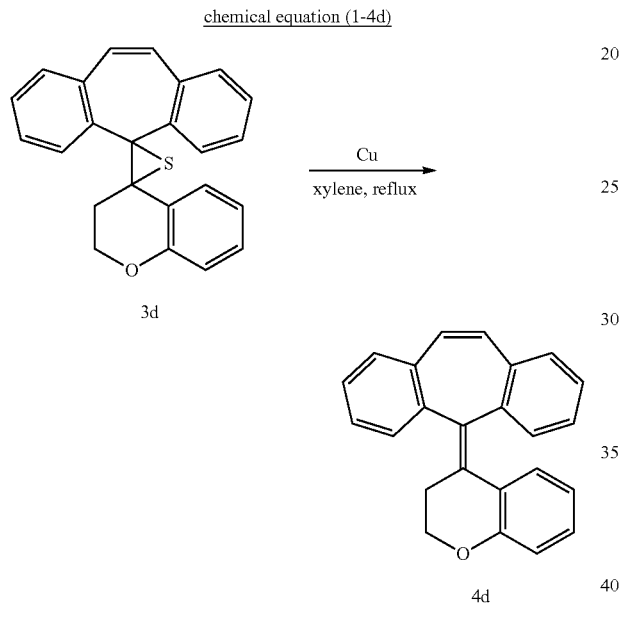

chemical equation (1-4d)

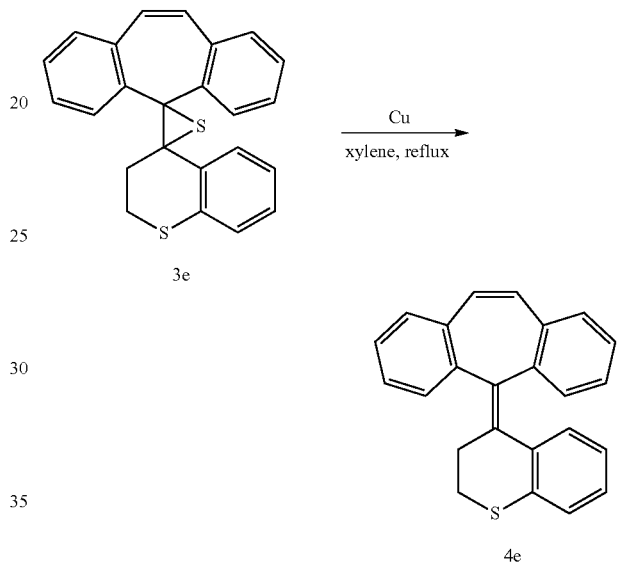

chemical equation (1-4e)

Example 4e: Synthesis of Compound 4e (4-(5H-dibenzo[a,d][7]annulen-5-ylidene)thiochromane)

A stir bar was placed in a 50 mL, two-necked flask, and the flask was then equipped to a condenser, followed by being dried under vacuum. The compound 3e (60.7 mg, 0.164 mmol) dissolved in anhydrous dimethylbenzene (10 mL) was added into the 50 ml flask, followed by adding dried copper powder (105.3 mg, 1.64 mmol). The 50 ml flask containing the reaction mixture was then put in an oil bath at 180° C. for reflux. The reaction mixture was refluxed for 2 hours, and then the red-brown copper powder was found to become black copper sulfide. After the reaction was completed, a crude product was collected with a filtering funnel which was fitted inside with a filter paper. The flask was washed by ether to collect the residual crude product in the flask. After filtration and condensation with a rotary evaporator, a white solid was obtained. The obtained solid was then purified by column chromatography by using a mixture of ether/n-hexane (1/100) as an eluent, and followed by being recrystallized with n-hexane to obtain the compound 4e (54.5 mg, yield: 99%). The above reaction is represented by the chemical equation (1-4e).

Example 5: Synthesis of Compound 5 (5-(3,4-dihydro-2H-naphthalen-1-ylidene)-5H-dibenzo[a,d]cycloheptene-10,11-dione)

A stir bar was placed in a two-necked, round-bottomed flask, and the flask was then installed to a reflux condenser system. The compound 4a (320.43 mg, 1 mmol) and benzeneseleninic anhydride (BSA, 720.26 mg, 2 mmol) were added into the flask and dissolved in chlorobenzene (10 mL), followed by refluxing for 5 hours until the color of the solution turned to orange-red. The reaction mixture was filtered by a filtering funnel, which was fitted inside with silica gel (3 cm height) in advance. The reaction mixture was filtered with n-hexane first to remove diphenyl diselenide, and all the crude products were then filtered by washing with dichloromethane, followed by being purified by column chromatography by using a mixture of EtOAc/hexane (1/30) as an eluent to obtain the compound 5 (158 mg, yield: 45%). The above reaction is represented by the chemical equation (1-5).

Spectral data as follow: M.W.: 350.41; $^1$H NMR (400 MHz, CDCl$_3$) δ 7.89 (d, J=5.3, 1H), 7.82 (d, J=7.6, 1H), 7.56 (t, J=7.5, 1H), 7.48 (t, J=7.6, 2H), 7.33-7.30 (m, 2H), 7.08-7.01 (m, 3H), 6.69 (t, J=7.2, 1H), 6.45 (d, J=7.8, 1H), 2.97-2.91 (m, 2H), 2.74-2.70 (m, 1H), 2.06-2.00 (m, 3H); $^{13}$C NMR (100 MHz, CDCl$_3$) δ 189.19, 188.63, 143.13, 142.39, 142.06, 139.46, 135.58, 135.47, 133.74, 132.83, 131.10, 130.73, 129.11, 129.04, 128.60, 128.00, 127.93, 127.83, 127.70, 124.70, 29.44, 29.20, 23.68; TLC R$_f$=0.20 (EtOAc/hexanes, 1/30).

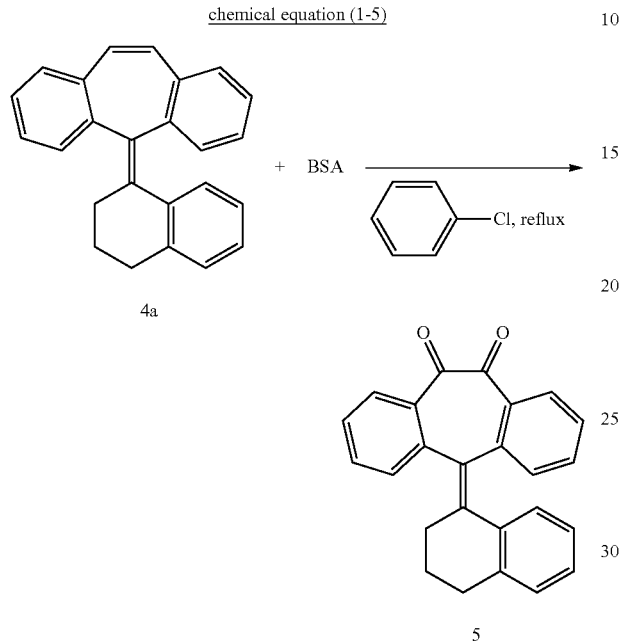

chemical equation (1-5)

4a

5

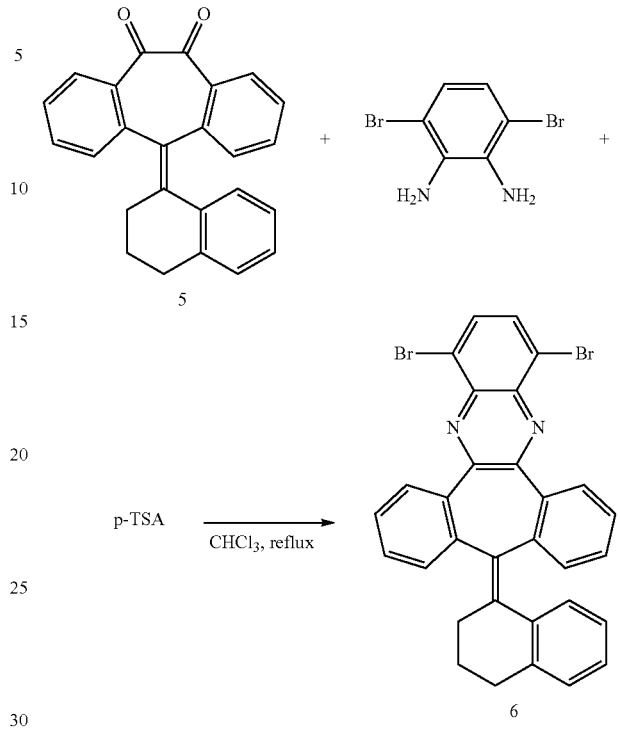

chemical equation (1-6)

5

6

Example 6: Synthesis of Compound 6 (1,4-dibromo-quinoxaline-5-(3,4-dihydro-2H-naphthalen-1-ylidene)-5H-dibenzo[a,d]cycloheptene)

A two-necked, round-bottomed flask was installed to a reflux condenser system. The compound 5 (350.41 mg, 1 mmol) and 3,6-dibromobenzene-1,2-diamine (397 mg, 1.5 mmol) were added into the flask and dissolved in chloroform (10 mL), followed by adding p-TSA (p-toluene sulfonic acid, 8.61 mg, 5 mol %) into the flask. After the reaction mixture was refluxed for 8 hours, the mixture was extracted by dichloromethane and H$_2$O (30 mL/30 mL) and the organic layer was then collected. The collected organic layer was dried by adding magnesium sulfate, followed by being purified by column chromatography by using a mixture of dichloromethane/n-hexane (1/2) as an eluent to obtain the compound 6 (464 mg, yield: 80%). The above reaction is represented by the chemical equation (1-6).

Spectral data as follow: M.W.: 580.31; $^1$H NMR (400 MHz, CDCl$_3$) δ 8.27 (d, J=7.7, 1H), 8.19 (d, J=7.5, 1H), 7.96 (s, 2H), 7.54-7.41 (m, 4H), 7.30 (t, J=7.4, 1H), 7.08-7.00 (m, 3H), 6.72 (t, J=7.5, 1H), 6.51 (d, J=7.8, 1H), 2.96-2.86 (m, 3H), 2.07-1.90 (m, 3H); $^{13}$C NMR (100 MHz, CDCl$_3$) δ 135.24, 133.18, 132.06, 131.34, 130.21, 129.40, 128.28, 127.79, 127.38, 127.11, 126.88, 125.79, 125.01, 124.63, 29.25, 27.77, 22.45; TLC R$_f$=0.50 (CH$_2$Cl$_2$/hexanes, 1/2).

Example 7a: Synthesis of Compound 7a (1,4-di-(phenyl-methoxyl)-quinoxaline-5-(3,4-dihydro-2H-naphthalen-1-ylidene)-5H-dibenzo[a,d]cycloheptene)

A two-necked, round-bottomed flask was installed to a reflux condenser system. The compound 6 (290 mg, 0.5 mmol), 4-methoxy-phenyl bonoic acid (227.94 mg, 1.5 mmol) and Na$_2$CO$_3$ (126 mg, 1.5 mmol) were added into the flask, and then the mixture was dissolved in a co-solvent system containing ethylene glycol dimethyl ether (EGDME) and H$_2$O (5 mL, EGDME:H$_2$O=4:1), followed by adding Pd(PPh$_3$)$_4$ (17 mg, 3 mol %). After the reaction mixture was refluxed for 8 hours, the mixture was extracted by dichloromethane/H$_2$O (30 mL/30 mL) and the organic layer was collected. The collected organic layer was dried by adding magnesium sulfate, followed by being purified by column chromatography by using a mixture of dichloromethane/n-hexane (1/1) as an eluent to obtain the compound 7a (229 mg, yield: 73%). The above reaction is represented by the chemical equation (1-7a).

Spectral data as follow: M.W.: 636.78; m.p.: 289° C.; T$_g$=127° C.; T$_d$=398° C.; $^1$H NMR (400 MHz, CDCl$_3$) δ 8.06 (t, J=8.0, 2H), 7.88-7.85 (m, 6H), 7.44 (t, J=5.1, 1H), 7.39 (t, J=6.8, 2H), 7.30 (t, J=6.5, 1H), 7.21 (t, J=6.3, 1H), 7.11-7.09 (m, 4H), 7.08-7.02 (m, 3H), 6.65 (d, J=7.4, 1H), 6.49 (d, J=7.8, 1H), 3.94 (s, 3H), 3.91 (s, 3H), 2.93-2.83 (m, 3H), 2.04-1.96 (m, 2H), 1.88-1.84 (m, 1H); $^{13}$C NMR (100 MHz, CDCl$_3$) δ 159.19, 159.14, 150.85, 150.72, 144.77, 139.07, 136.56, 132.08, 132.03, 131.21, 131.14, 131.01, 129.70, 129.58, 129.53, 129.40, 129.17, 128.30, 127.42, 127.09, 126.96, 126.88, 124.48, 113.54, 113.40, 55.34, 29.59, 28.75, 23.95; TLC R$_f$=0.60 (CH$_2$Cl$_2$/hexanes, 1/1); Elemental Analysis. Calcd for C$_{45}$H$_{34}$N$_2$O$_2$: C, 85.15; H, 5.40; N, 4.41; O, 5.04. found: C, 85.17; H, 5.34; N, 4.10.

chemical equation (1-7a)

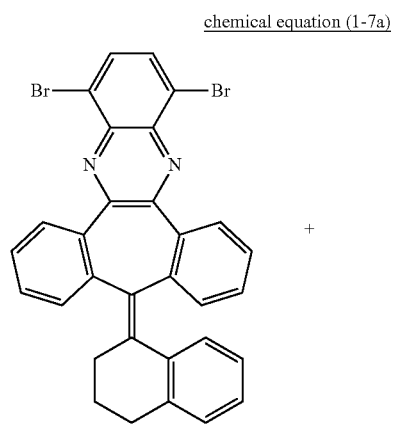

Spectral data as follow: M.W.: 632.79; m.p.: 292° C.; $T_g$=108° C.; $T_d$=385° C.; $^1$H NMR (400 MHz, CDCl$_3$) δ 7.61 (t, J=7.3, 2H), 7.59 (m, 1H), 7.36 (t, J=7.0, 1H), 7.32-7.31 (m, 1H), 7.24-7.14 (m, 7H), 7.01-6.84 (m, 10H), 6.64 (t, J=7.0, 1H), 6.35 (d, J=7.9, 1H), 3.60 (s, 6H), 2.91-2.79 (m, 3H), 2.04-1.95 (m, 3H); $^{13}$C NMR (100 MHz, CDCl$_3$) δ 151.02, 144.51, 142.97, 136.67, 131.77, 131.29, 129.74, 129.42, 129.16, 128.89, 128.81, 128.28, 127.37, 126.91, 126.83, 126.79, 126.03, 124.52, 118.90, 118.57, 116.95, 116.35, 112.43, 41.55, 41.41, 29.61, 28.76, 23.97; TLC R$_f$=0.60 (CH$_2$Cl$_2$/hexanes, 1/1); Elemental Analysis. Calcd for C$_{45}$H$_{36}$N$_4$: C, 85.41; H, 5.73; N, 8.85. found: C, 84.96; H, 5.57; N, 8.56.

chemical equation (1-7b)

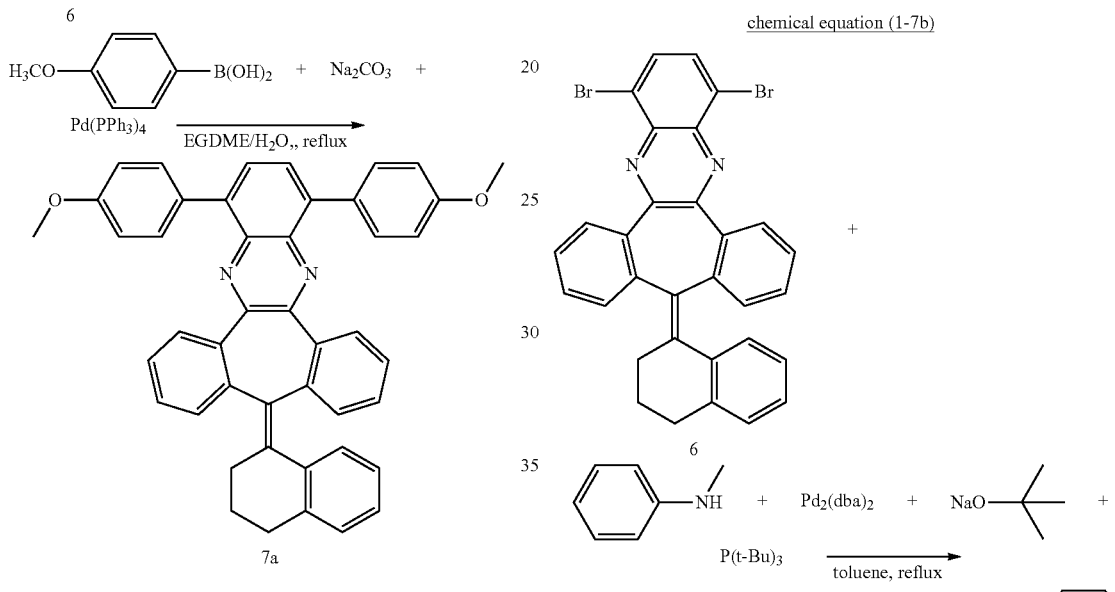

Example 7b: Synthesis of Compound 7b (1,4-di-(n-phenyl,n-methyl-amine)-quinoxaline-5-(3,4-dihydro-2H-naphthalen-1-ylidene)-5H-dibenzo[a,d]cycloheptene)

A stir bar was placed in a 50 mL, two-necked flask, and the flask was then equipped to a condenser, followed by being dried under vacuum. The compound 6 (580 mg, 1.0 mmol), methyl-phenyl-amine (225 mg, 2.1 mmol), Pd(dba)$_2$ (20 mg, 0.04 mmol) and sodium tert-butoxide (288 mg, 3.0 mmol) were added into the flask, and then the mixture was dissolved in toluene (20 mL, dehydrated by sodium in advance), followed by injecting (t-Bu)$_3$P (8-12 mg, 0.04-0.06 mmol). After the reaction mixture was refluxed for 36 hours, deionized H$_2$O (30 mL) was added to quench the reaction. The mixture was then extracted by a mixture of dichloromethane/H$_2$O (30 mL/30 mL) and the organic layer was then collected. The collected organic layer was dried by adding magnesium sulfate, followed by being purified by column chromatography by using a mixture of dichloromethane/n-hexane (1/1) as an eluent to obtain the compound 7b (yield: 70%). The above reaction is represented by the chemical equation (1-7b).

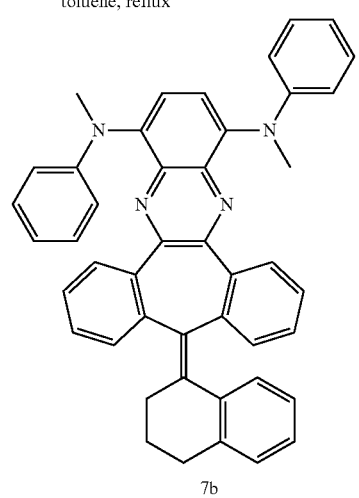

Example 7c: Synthesis of Compound 7c (1,4-di-(phenyl-N,N-diphenyl-amine)-quinoxaline-5-(3,4-dihydro-2H-naphthalen-1-ylidene)-5H-dibenzo[a,d]cycloheptene)

A two-necked, round-bottomed flask was installed to a reflux condenser system. The compound 6 (290 mg, 0.5 mmol), diphenyl-p-tolyl-amine (227.94 mg, 1.5 mmol) and Na$_2$CO$_3$ (126 mg, 1.5 mmol) were added into the flask, and then the mixture was dissolved in a co-solvent system containing ethylene glycol dimethyl ether (EGDME) and H$_2$O (5 mL, EGDME:H$_2$O=4:1), followed by adding Pd(PPh$_3$)$_4$ (17 mg, 3 mol %). After the reaction mixture was refluxed for 8 hours, the mixture was extracted by dichloromethane/H$_2$O (30 mL/30 mL) and the organic layer was collected. The collected organic layer was dried by adding magnesium sulfate, followed by being purified by column chromatography by using a mixture of dichloromethane/n-hexane (1/1) as an eluent to obtain the compound 7c (229 mg, yield: 80%). The above reaction is represented by the chemical equation (1-7c).

Spectral data as follow: M.W.: 911.14; m.p.: 466° C.; T$_g$=146° C.; T$_d$=547° C.; $^1$H NMR (400 MHz, CDCl$_3$) δ 8.07 (d, J=8.5, 2H), 7.92-7.91 (m, 2H), 7.82 (dd, J=8.5, 2.2, 4H), 7.47 (t, J=6.8, 1H), 7.40 (t, J=6.5, 2H), 7.31-7.27 (m, 8H), 7.23-7.21 (m, 9H), 7.09-7.01 (m, 8H), 6.66 (d, J=7.4, 1H), 6.50 (d, J=7.8, 1H), 2.93-2.85 (m, 3H), 2.00-1.99 (m, 2H), 1.86 (m, 1H); $^{13}$C NMR (100 MHz, CDCl$_3$) δ 150.64, 147.79, 147.19, 139.08, 136.74, 131.76, 131.67, 131.04, 129.75, 129.43, 129.33, 129.22, 128.33, 126.89, 124.83, 124.75, 124.52, 124.19, 123.05, 122.61, 41.38, 31.62, 29.61, 29.09, 28.87, 24.01, 22.65, 14.15, 11.46; TLC R$_f$=0.65 (CH$_2$Cl$_2$/hexanes, 1/1); High Resolution-MS calcd for C$_{67}$H$_{48}$N$_4$ 909.1248, found: 909.1249.

chemical equation (1-7c)

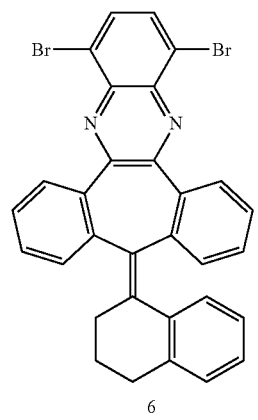

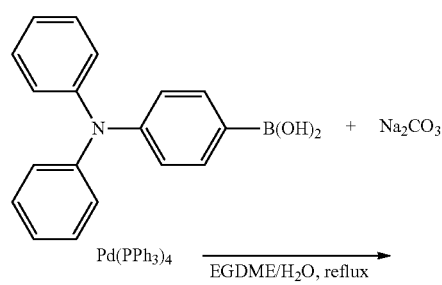

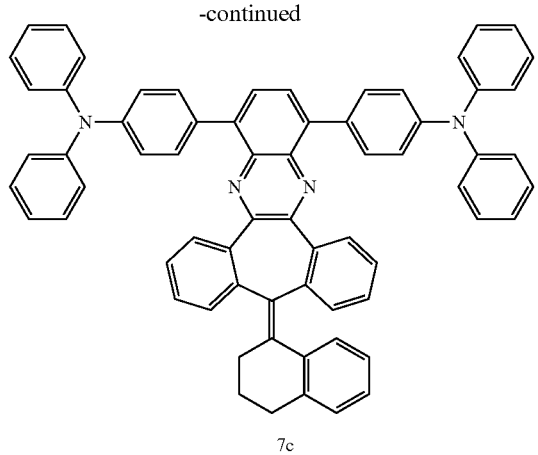

Example 8: Synthesis of Compound 14 (4-(naphthalen-2-yl)butanoic acid)

A two-necked flask was dried under vacuum, followed by being filled with nitrogen gas. The compound 13 (228 mg, 1 mmol), hydrazine (0.05 mL, 1 mmol) and potassium hydroxide (190 mg, 1.3 mmol) were dissolved in bis(2-hydroxy-ethyl) ether (1.7 mL), followed by heating to 100° C. for 100 minutes in an oil bath. Then, the flask was removed from the oil bath, followed by vacuum for 2-3 hours. The flask was then filled with nitrogen gas and heated to 230° C. for 5 hours. After the flask was cooled down, it was then placed in an ice bath. The reaction mixture was then washed by hydrochloric acid (15 mL, 6N) for several times to obtain a crude product. The crude product was then extracted by ether (100 mL) to collect the organic layer. The collected organic layer was dried by adding magnesium sulfate, followed by condensation by a rotary evaporator. The resulting product was then recrystallized with cyclohexane to obtain the compound 14 (90 mg, yield: 42%). The above reaction is represented by the chemical equation (2-1).

Spectral data as follow: M.W.: 214.26; $^1$H NMR (400 MHz, CDCl$_3$) δ 7.79 (t, J=8.5, 3H), 7.62 (s, 1H), 7.45-7.41 (m, 2H), 7.33 (d, J=8.2, 1H), 2.84 (t, J=7.4, 2H), 2.41 (t, J=7.4, 2H), 2.06 (t, J=7.4, 2H); $^{13}$C NMR (100 MHz, CDCl$_3$) δ 179.29, 138.69, 137.33, 133.63, 132.15, 128.82, 128.07, 127.63, 127.47, 127.20, 126.94, 126.65, 126.23, 125.99, 125.93, 125.54, 125.51, 125.28, 123.71, 35.16, 33.57, 33.26, 32.21, 26.09, 25.51.

chemical equation (2-1)

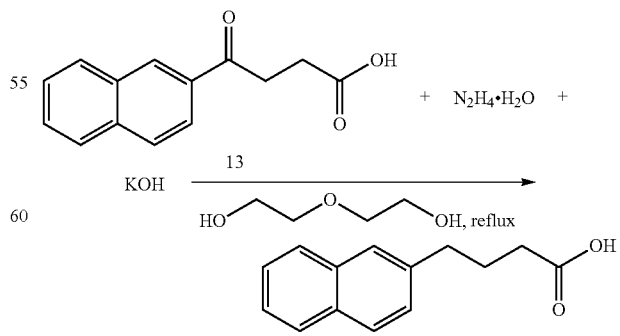

Example 9: Synthesis of Compound 15 (2,3-dihydrophenanthren-4(1H)-one)

An addition funnel was installed on a tri-necked flask. The flask was dried under vacuum, followed by being filled with nitrogen gas. The compound 14 (214 mg, 1 mmol) was dissolved in benzene (5 mL, dehydrated and purified in advance), followed by adding $PCl_5$ (270 mg, 1.3 mmol). After reacting at room temperature for 30 minutes, the flask was then placed in an ice bath. $SnCl_4$ (0.2 mL, 0.52 mg, 2 mmol) was added dropwisely through the addition funnel into the flask at 0° C. (about 20 minutes). After reacting for 1 hour at 0° C., the flask containing the reaction mixture was put in the ice bath. The reaction mixture was extracted by EtOAc (30 mL) to collect the organic layer. The collected organic layer was dried by adding magnesium sulfate, and then purified by column chromatography with a mixture of EtOAc and hexanes (1/10) as an eluent to obtain compound 15 (92 mg, yield: 47%). The above reaction is represented by the chemical equation (2-2).

Spectral data as follow: M.W.: 196.24; $^1$H NMR (400 MHz, $CDCl_3$) δ 9.40 (d, J=8.7, 1H), 7.92 (d, J=8.3, 1H), 7.80 (d, J=8.0, 1H), 7.62 (t, J=7.4, 1H), 7.49 (t, J=7.4, 1H), 7.32 (d, J=8.4, 1H), 3.13 (t, J=6.0, 2H), 2.79 (t, J=6.5, 2H), 2.23-2.17 (m, 2H); $^{13}$C NMR (100 MHz, $CDCl_3$) δ 200.46, 198.55, 146.75, 142.94, 135.75, 134.22, 132.83, 131.42, 130.05, 128.84, 128.80, 128.29, 127.34, 126.98, 126.95, 126.71, 125.84, 124.84, 122.79, 41.12, 38.40, 31.63, 25.65, 23.05, 22.79; TLC $R_f$=0.30 (EtOAc/hexanes, 1/10).

chemical equation (2-2)

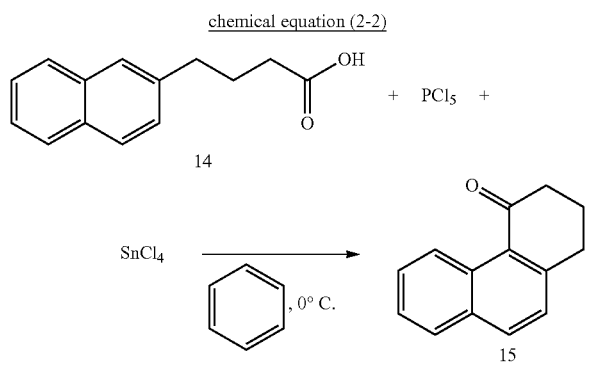

Example 10a: Synthesis of Compound 16a (1-(2,3-dihydrophenanthren-4(1H)-ylidene)hydrazine)

A 100 mL, single-neck flask was placed on a Dean-Stark trap and then dried under vacuum. Ethanol (30 mL) was added to the flask, followed by adding the compound 15 (196 mg, 1 mmol) and hydrazine monohydrate (0.87 mL, 18 mmol). The reaction mixture was refluxed for 6 hours at 120° C., and then the flask was removed from the reflux system and cooled down to room temperature. The ethanol was removed by the vacuum system and then the compound 16a (yield: 100%) was obtained. Because the product 16a tended to decompose easily, it was used for the following reactions without purification. The above reaction is represented by the chemical equation (2-3a).

Spectral data as follow: M.W.: 210.27; $^1$H NMR (200 MHz, $CDCl_3$) δ 9.10 (d, J=8.0, 1H), 7.82 (d, J=7.6, 1H), 7.72 (d, J=8.0, 1H), 7.48 (m, 2H), 7.29 (d, J=2.4, 1H), 2.84 (t, J=5.8, 2H), 2.64 (t, J=6.8, 2H), 1.97 (q, J=6.0, 2H).

chemical equation (2-3a)

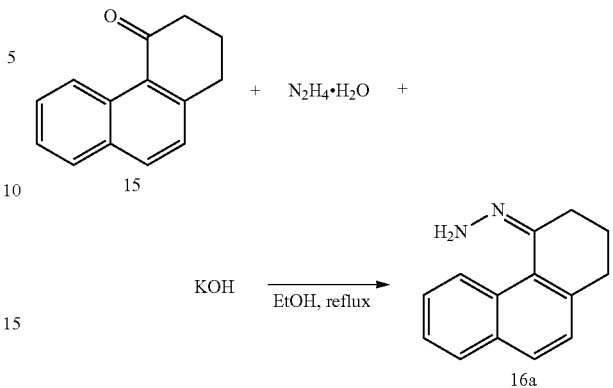

Example 11a: Synthesis of Compound 17a (Endo-(1,2,3,4,-tetratydro-1-phenanthrenyliden-2'-thirrane-3"-10,11-dihydro-5H-dibenzo[a,d]cycloheptene))

Each end (top and bottom) of a Schlenk tube was installed with a two-necked 50 ml flask which was then dried under vacuum. The compound 16a (210 mg, 1 mmol) dissolved in anhydrous dichloromethane (10 mL) was then transferred into the flask installed at bottom end of the Schlenk tube by a double-tipped needle. At −30° C., dried silver(I) oxide (695 mg, 3 mmol) and magnesium sulfate (1.24 g) were well mixed and then poured into the flask at bottom end of the Schlenk tube, followed by dropwisely addition of saturated potassium hydroxide solution (in methanol, 2.35 mL) into the flask at bottom end of the Schlenk tube. After reacting for 40 minutes at −30° C., the Schlenk tube was inverted to filter out the solid impurities (i.e., silver oxide and magnesium sulfate) and thus to collect the dark-red filtrate in the other two-necked flask. Then the flask containing the filtrate was placed at −30° C. The compound 2 (thioketone, 223 mg, 1 mmol) dissolved in anhydrous dichloromethane (10 mL, concentration: 0.1M) was slowly injected into the flask containing the filtrate with an air-tight syringe until no bubbles were produced in the solution and the color of the solution became light green (the color of compound 2). After reacting for 9 hours at −30° C., the reaction mixture was added with saturated, aqueous sodium bicarbonate solution (10 mL) to quench the reaction. The organic layer of the reaction mixture was then extracted with dichloromethane (150 mL). Then, the collected organic layer was dried by adding anhydrous magnesium sulfate, followed by filtration and condensation to obtain a condensed solution. The condensed solution was then purified by column chromatography by using a mixture of ether/n-hexane (1/100) as an eluent, so as to obtain a crude product. The crude product was recrystallized with a mixture of n-hexane/dichloromethane to obtain the compound 17a (235 mg, yield: 58%). The above reaction is represented by the chemical equation (2-4a).

Spectral data as follow: M.W.: 402.55; m.p.: 164-167° C.; $^1$H NMR: (400 MHz, $CDCl_3$) δ 9.37 (d, J=8.7, 1H), 7.75-7.68 (m, 2), 7.35-7.15 (m, 5H), 6.99-6.83 (m, 5H), 6.61 (t, J=7.0, 1H), 6.46 (d, J=7.3, 1H), 6.20 (d, J=11.7, 1H), 3.09-3.03 (m, 1H), 2.90-2.50 (m, 1H), 2.50-2.42 (m, 1H), 1.87-1.76 (m, 1H), 1.46-1.41 (m, 2H); $^{13}$C NMR (100 MHz, $CDCl_3$) δ 139.55, 138.55, 135.42 134.70, 134.60, 132.68, 131.80, 131.20, 130.87, 129.43, 128.57, 128.28, 127.92, 127.68, 127.58, 127.35, 126.94, 126.84, 126.38, 126.05, 126.01, 123.69, 123.47, 67.39, 58.36, 39.44, 31.10, 21.22; MS: (20 eV) 404 (9), 402 (M$^+$, 100), 369 (95), 247 (10), 221 (10), 191 (43); Analysis: (C$_{29}$H$_{22}$S (402.55)) Calcd: C, 86.53; H, 5.51; Found: C, 86.47; H, 5.59; TLC: R$_f$ 0.27 (hexane/ether, 100/1).

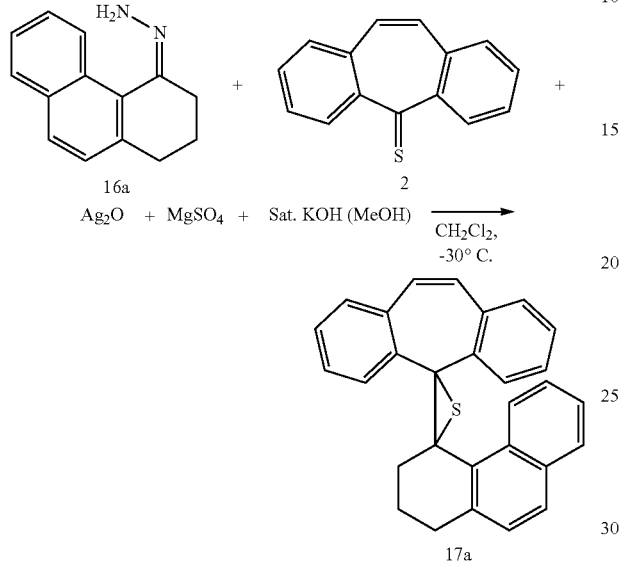

Example 12a: Synthesis of Compound 18a (5-(2,3-Dihydro-1H-phenanthren-4-ylidene)-5H-dibenzo[a,d]cycloheptene)

A stir bar was placed in a two-necked 50 mL flask, and the flask was then equipped to a condenser, followed by being dried under vacuum. The compound 17a (402 mg, 1 mmol) was dissolved in anhydrous dimethylbenzene (20 mL) and followed by adding dried copper powder (635 mg, 10 mmol) into the flask. The flask was then put in an oil bath at 150° C. for reflux. The reaction mixture was refluxed for 2 hours, and then the red-brown copper powder became to black copper sulfide. After the reaction was completed, a crude product was collected with a filtering funnel which was fitted inside with a filter paper. The flask was washed by anhydrous ether to collect the residual crude product in the flask. After filtration and condensation with a rotary evaporator, a white solid was obtained. The obtained solid was then recrystallized with a mixture of n-hexane/dichloromethane to obtain the compound 18a (360 mg, yield: 98%). The above reaction is represented by the chemical equation (2-5a).

Spectral data as follow: M.W.: 370.48; $^1$H NMR (400 MHz, CDCl$_3$) δ 7.53-7.48 (m, 3H), 7.62-7.32 (m, 3H), 7.31-7.24 (m, 2H), 7.07-7.03 (m, 4H), 6.94 (t, J=8.0, 1H), 6.70 (t, J=8.0, 1H), 6.50 (t, J=8.0, 1H), 6.30 (d, J=8.0, 1H), 2.95-2.87 (m, 3H), 2.24-2.21 (m, 1H), 1.89-1.78 (m, 2H); $^{13}$C NMR (100 MHz, CDCl$_3$) δ 141.24, 138.40, 138.11, 136.66, 136.46, 135.27, 135.09, 134.33, 131.70, 131.69, 131.60, 128.44, 128.25, 128.12, 128.09, 127.90, 127.24, 126.74, 126.49, 125.85, 125.75, 125.62, 124.39, 124.10, 29.16, 27.13. 22.45; MS (20 eV) 370 (M$^+$, 100), 192 (14); Elemental Analysis. Calcd for C$_{29}$H$_{22}$: C, 94.01; H, 5.99; Found: C, 93.75; H, 6.33; TLC: R$_f$ 0.30 (hexane/ether, 100/1); UV λ$_{max}$: 289 nm (ε 20937, in hexane).

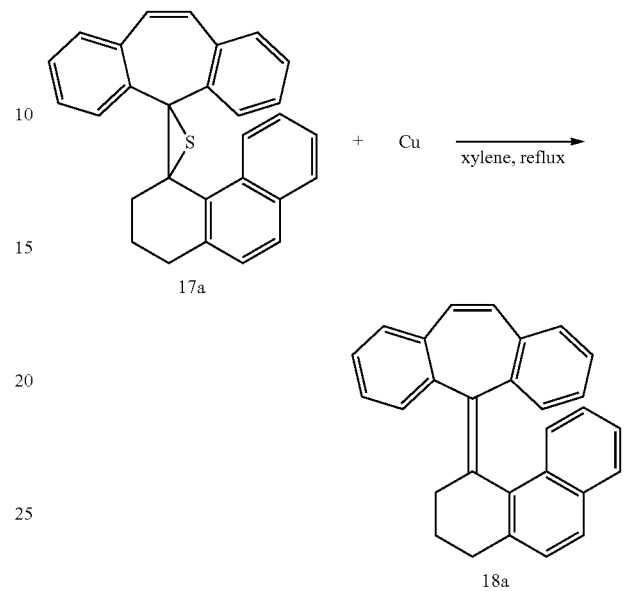

Example 11b: Synthesis of Compound 17b (3″,4″-dihydro-2″H-dispiro[dibenzo[a,d][7]annulene-5,2′-thiirane-3′,1″-phenanthrene])

Each end (top and bottom) of a Schlenk tube was installed with a two-necked 50 ml flask which was then dried under vacuum. The compound 16b (237.1 mg, 1.12 mmol) dissolved in anhydrous dichloromethane (10 mL) was then transferred into the flask installed at bottom end of the Schlenk tube by a double-tipped needle. At −30° C., dried silver(I) oxide (389.7 mg, 1.7 mmol) and magnesium sulfate (0.73 g) were well mixed and then poured into the flask at bottom end of the Schlenk tube, followed by dropwisely injected saturated potassium hydroxide solution (in methanol, 0.87 mL) into the flask at bottom end of the Schlenk tube. After reacting for 40 minutes at −30° C., the Schlenk tube was inverted to filter out the solid impurities (i.e., silver oxide and magnesium sulfate) and thus to collect the dark-red filtrate in the other two-necked flask. Then the flask containing the filtrate was placed at 0° C. The compound 2 (thioketone, 57.2 mg, 0.26 mmol) dissolved in anhydrous dichloromethane (4.6 mL, concentration: 0.1M) was slowly injected into the flask containing the filtrate with an air-tight syringe until no bubbles were produced in the solution and the color of the solution became light green (the color of compound 2). After reacting for 10 hours at 0° C., the reaction mixture was added with saturated, aqueous sodium bicarbonate solution (10 mL) to quench the reaction. The organic layer of the reaction mixture was then extracted with ether (150 mL) for three times. Then, the collected organic layer was dried by adding anhydrous magnesium sulfate, followed by filtration and condensation to obtain a condensed solution. The condensed solution was then purified by column chromatography by using a mixture of ether/n-hexane (1/100) as an eluent, so as to obtain a crude product. The crude product was recrystallized with n-hexane to obtain the compound 17b (54.8 mg, yield: 54%). The above reaction is represented by the chemical equation (2-4b).

Spectral data as follow: m.p.: 224-225° C.; $^1$H NMR: (400 MHz, CDCl$_3$) 7.98 (d, J=7.5, 1H), 7.91 (d, J=8.5, 1H), 7.77 (d, J=7.8, 1H), 7.56 (d, J=7.8, 1H), 7.43-7.33 (m, 4H), 7.30-7.24 (m, 2H), 7.13 (t, J=7.3, 1H), 6.95 (d, J=11.7, 1H), 6.95 (d, J=8.7, 1H), 6.62 (d, J=9, 1H), 6.45 (d, J=11.7, 1H), 3.20 (dt, J=16.8, 4, 1H), 3.08 (dt, J=16.8, 1H), 2.12-2.01 (m, 2H), 1.78-1.76 (m, 1H), 1.48-1.43 (m, 1H); $^{13}$C NMR: (100 MHz, CDCl$_3$) 138.83, 136.55, 134.74, 134.68, 133.99, 132.21, 131.50, 131.37, 130.58, 130.48, 129.26, 128.38, 128.00, 128.00, 127.61, 126.95, 126.78, 126.49, 126.42, 125.39, 125.22, 123.42, 123.16, 58.44, 35.26, 29.28, 26.00, 22.02; MS: (20 eV) 404 (8), 402 (M$^+$, 100), 369 (23), 191 (15); TLC: R$_f$0.53 (hexane/ether, 100/1).

Spectral data as follow: mp: 198-199° C.; M.W.: 370.49; $^1$H NMR (400 MHz, CDCl$_3$) δ 7.92 (d, J=8.0, 1H), 7.57 (d, J=8.0, 1H), 7.41-6.95 (m, 12H), 6.87 (d, J=8.0, 1H), 6.34 (d, J=8.0, 1H), 3.39-3.18 (m, 2H), 2.86 (d, J=12.0, 1H), 2.5-2.16 (m, 2H), 1.86 (t, J=12.0, 1H); $^{13}$C NMR (100 MHz, CDCl$_3$) δ 140.53, 138.89, 136.51, 134.40, 133.71, 133.56, 132.18, 132.17, 131.88, 131.30, 131.04, 129.11, 128.38, 128.09, 128.04, 127.91, 127.76, 127.46, 126.29, 126.15, 125.56, 125.22, 123.81, 123.23, 28.44, 26.30, 24.87; MS (20 eV) 370 (M$^+$, 100); Elemental Analysis. Calcd for C$_{29}$H$_{22}$: C, 94.01; H, 5.99; Found: C, 94.00; H, 5.98; TLC: R$_f$0.23 (hexane); UV λ$_{max}$: 273 nm (ε 89580, in hexane).

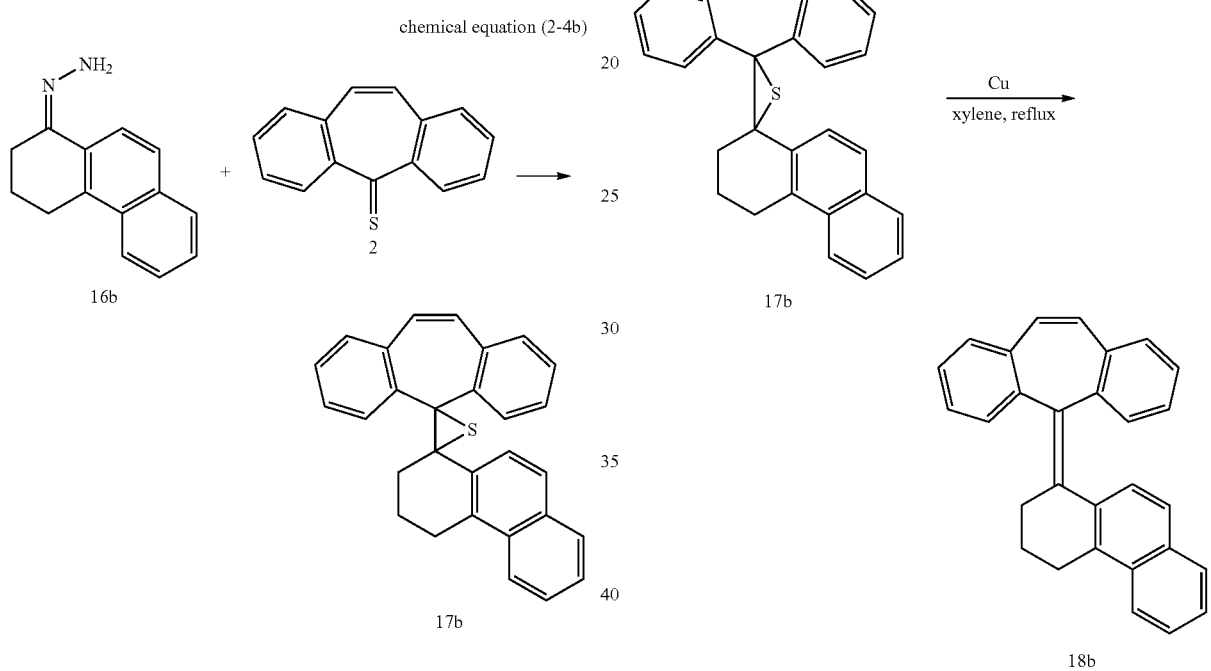

chemical equation (2-4b)

16b

2

17b

17b

18b chemical equation (2-5b)

Example 12b: Synthesis of Compound 18b (5-(3,4-dihydrophenanthren-1 (2H)-ylidene)-5H-dibenzo[a,d][7]annulene)

A stir bar was placed in a two-necked 50 mL flask, and the flask was then equipped to a condenser, followed by being dried under vacuum. The compound 17b (55.5 mg, 0.13 mmol) was dissolved in anhydrous dimethylbenzene (10 mL) and followed by adding dried copper powder (88.2 mg, 1.37 mmol) into the flask. The flask was then put in an oil bath at 180° C. for reflux. The reaction mixture was refluxed for 2 hours, and then the red-brown copper powder became to black copper sulfide. After the reaction was completed, a crude product was collected with a filtering funnel which was fitted inside with a filter paper. The flask was washed by anhydrous ether to collect the residual crude product in the flask. After filtration and condensation with a rotary evaporator, a white solid was obtained. The obtained solid was then purified by column chromatography by using n-hexane as an eluent and followed by being recrystallized with n-hexane to obtain the compound 18b (43.8 mg, yield: 91%). The above reaction is represented by the chemical equation (2-5b).

Example 13: Synthesis of Compound 19 (5-(2,3-dihydro-1H-phenanthren-4-ylidene)-5H-dibenzo[a,d]cycloheptene-10,11-dione)

A stir bar was placed in a two-necked, round-bottomed flask, and the flask was then installed to a reflux condenser system. The compound 18a (370 mg, 1 mmol) and benzeneseleninic anhydride (BSA, 720.26 mg, 2 mmol) were added into the flask and dissolved in chlorobenzene (10 mL), followed by refluxing for 5 hours until the color of the solution turned to orange-red. The reaction mixture was filtered by a filtering funnel, which was fitted inside with silica gel (3 cm height) in advance. The reaction mixture was filtered and washed with n-hexane first to remove diphenyl diselenide, and all the crude products were then filtered with dichloromethane, followed by being purified by column chromatography by using a mixture of EtOAc/hexane (1/30) as an eluent to obtain the compound 19 (160 mg, yield: 40%). The above reaction is represented by the chemical equation (2-6).

Spectral data as follow: M.W.: 400.46; $^1$H NMR (400 MHz, CDCl$_3$) δ 8.20 (d, J=8.4, 1H), 7.85-7.84 (m, 1H), 7.73-.7.70 (m, 1H), 7.68-7.59 (m, 2H), 7.50-7.46 (m, 2H), 7.33-7.28 (m, 3H), 7.25-7.14 (m, 3H), 6.95-6.93 (m, 2H), 6.79 (t, J=5.8, 1H), 6.53 (t, J=6.0, 1H), 6.39 (d, J=7.6, 1H), 6.24 (d, J=7.7, 1H), 3.07-3.03 (m, 2H), 2.94-2.87 (m, 1H), 2.28 (m, 1H), 2.15-2.12 (m, 1H), 2.11-2.08 (m, 1H); $^{13}C$ NMR (100 MHz, CDCl$_3$) δ 189.19, 188.63, 143.13, 142.06, 139.46, 135.58, 135.47, 133.74, 132.83, 131.10, 130.73, 129.11, 129.04, 128.60, 128.00, 127.93, 127.83, 127.70, 124.70, 29.44, 29.20, 23.68; TLC R$_f$=0.33 (EtOAc/hexanes, 1/30).

128.28, 127.79, 127.38, 127.11, 126.88, 125.79, 125.01, 124.63, 29.25, 27.77, 22.45; TLC R$_f$=0.50 (CH$_2$Cl$_2$/Hexanes, 1/2).

chemical equation (2-6)

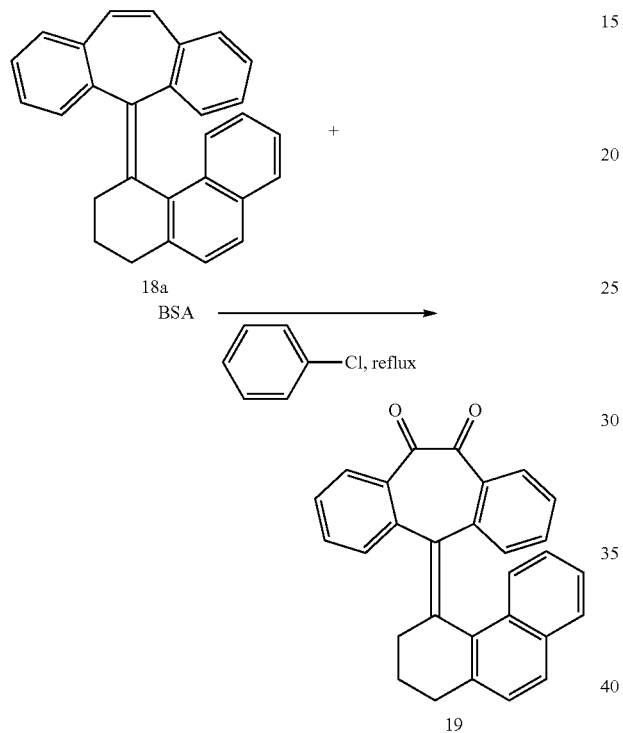

chemical equation (2-7)

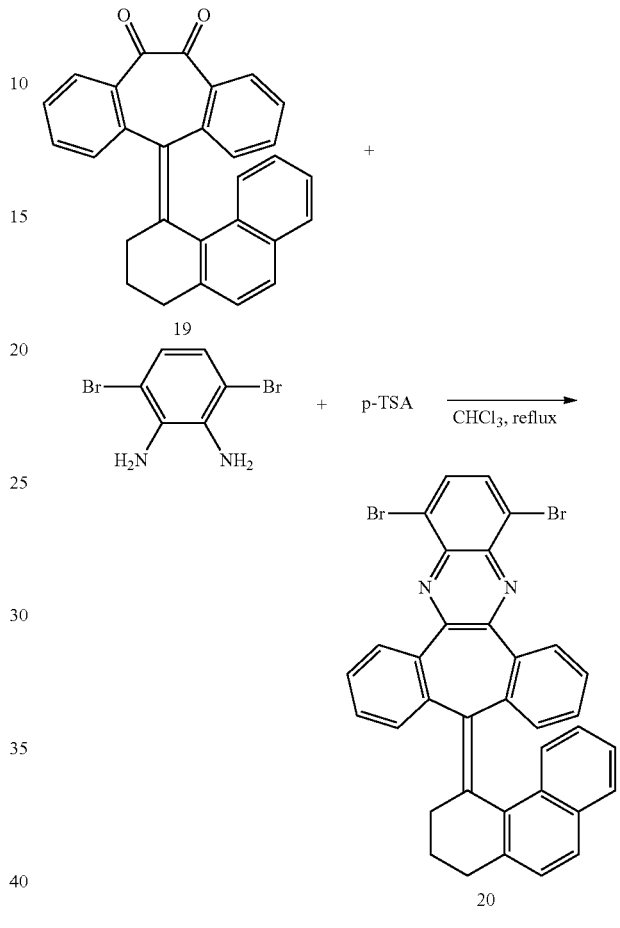

Example 14: Synthesis of Compound 20 (1,4-di-bromo-quinoxaline-5-(2,3-dihydro-1H-phenanthren-4-ylidene)-5H-dibenzo[a,d]cycloheptene)

A two-necked, round-bottomed flask was installed to a reflux condenser system. The compound 19 (400 mg, 1 mmol) and 3,6-dibromobenzene-1,2-diamine (397 mg, 1.5 mmol) were dissolved by chloroform (10 mL), followed by addition of p-TSA (p-toluene sulfonic acid, 8.61 mg, 5 mol %). After the reaction mixture was refluxed for 8 hours, it was extracted with a mixture of dichloromethane/H$_2$O (30 mL/30 mL) to collect the organic layer. The collected organic layer was dried by adding magnesium sulfate, followed by being purified by column chromatography by using a mixture of dichloromethane and hexanes (1/2) to obtain the compound 20 (472 mg, yield: 75%). The above reaction is represented by the chemical equation (2-7).

Spectral data as follow: M.W.: 630.37; 1H NMR (200 MHz, CDCl$_3$) δ 8.39-8.34 (m, 1H), 8.04-7.96 (m, 3H), 7.58-7.50 (m, 5H), 7.20-7.17 (m, 1H), 7.16-7.12 (m, 4H), 6.79 (t, J=7.6, 1H), 6.44 (d, J=7.6, 1H), 3.06-3.04 (m, 3H), 2.33-2.32 (m, 1H), 1.99-1.93 (m, 2H); $^{13}C$ NMR (100 MHz, CDCl$_3$) δ 135.24, 133.18, 132.06, 131.34, 130.21, 129.40,

Example 15: Synthesis of Compound 21 (1,4-di-phenyl-methoxyl-quinoxaline-5-(2,3-dihydro-1H-phenanthren-4-ylidene)-5H-dibenzo[a,d]cycloheptene)

A two-necked, round-bottomed flask was installed to a reflux condenser system. The compound 20 (315 mg, 0.5 mmol), 4-methoxy-phenyl bonoic acid (227.94 mg, 1.5 mmol) and Na$_2$CO$_3$ (126 mg, 1.5 mmol) were added into the flask, and then the mixture was dissolved in ethylene glycol dimethyl ether/H$_2$O solution (5 mL, EGDME/H$_2$O=4:1), followed by adding Pd (PPh$_3$)$_4$ (17 mg, 3 mol %). After the reaction mixture was refluxed for 8 hours, it was extracted with a mixture of dichloromethane/H$_2$O (30 mL/30 mL) to collect the organic layer. The organic layer was dried by adding magnesium sulfate, followed by being purified by column chromatography by using a mixture of dichloromethane/hexanes (1/1) as an eluent to obtain the compound 21 (499 mg, yield: 73%). The above reaction is represented by the chemical equation (2-8).

Spectral data as follow: M.W.: 684.27; m.p.: 400° C.; T$_g$=137° C.; 1H NMR (400 MHz, CDCl$_3$) δ 8.24 (d, J=7.3, 1H), 8.10 (d, J=8.6, 2H), 8.02-7.94 (m, 3H), 7.81 (d, J=7.8, 1H), 7.56 (d, J=8.2, 1H), 7.51-7.49 (m, 4H), 7.14-7.11 (m, 4H), 6.97-6.93 (m, 3H), 6.71 (t, J=7.6, 1H), 6.46 (t, J=7.8, 1H), 6.39 (d, J=7.4, 1H), 3.96 (s, 3H), 3.93 (s, 3H), 3.07-2.96 (m, 3H), 2.32 (m, 1H), 1.88-1.85 (m, 2H); $^{13}$C NMR (100 MHz, CDCl$_3$) δ 159.30, 159.21, 150.97, 144.84, 143.34, 136.22, 132.09, 131.30, 130.71, 129.73, 129.49, 129.30, 128.51, 128.16, 127.42, 127.13, 126.89, 126.59, 125.79, 125.62, 124.84, 113.63, 113.33, 55.39, 29.69, 29.21, 27.65, 22.36; TLC R$_f$=0.50 (CH$_2$Cl$_2$/hexanes, 1/1), High Resolution-MS calcd for C$_{49}$H$_{36}$N$_2$O$_2$: 684.2777, found: 684.2770.

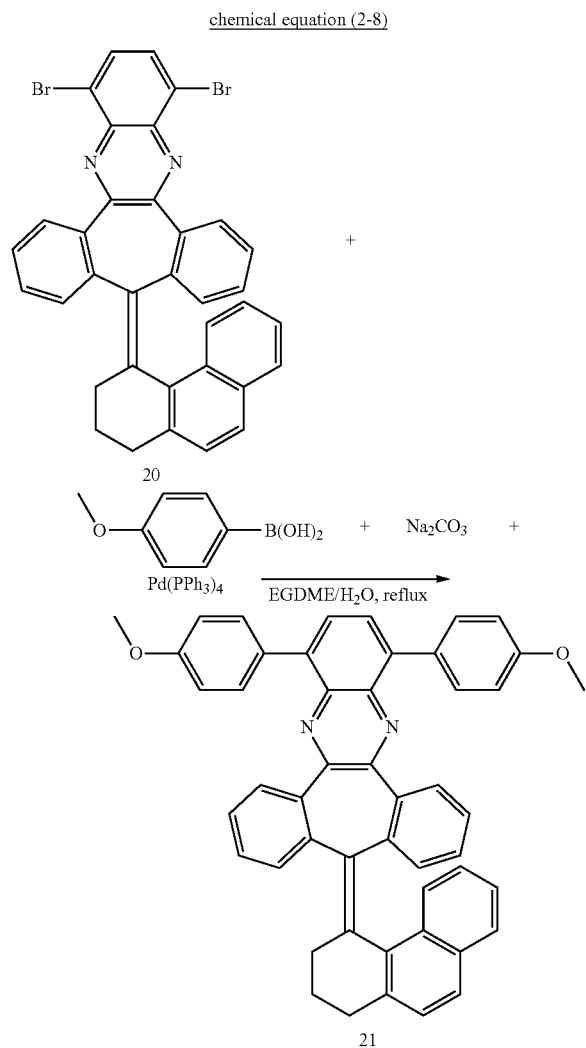

chemical equation (2-8)

In addition, the person having an ordinary skill in the art can understand that they can combine the reaction schemes shown above and/or substitute the starting materials in the above-listed examples to synthesis a series of compounds with quinoxaline-fused dibenzosuberane based helicenes which are represented by General Formula (1). For example, the compound 4a in chemical equation (1-5) can be replaced with any one of the compounds 4b to 4e synthesized in the Examples 4b to 4e, to synthesize the compounds which have the upper panel fragments similar to the compound 7a, 7b, or 7c but have the lower panel fragments corresponding to those in the compounds 4b to 4e, respectively according to the reaction schemes represented by the chemical equations (1-5) to (1-7a), (1-5) to (1-7b) or (1-5) to (1-7c). On the other hand, the compound 18a in chemical equation (2-6) can be replaced by the compound 18b, which is synthesized in the Example 12, to synthesize the compound which has an upper panel fragment similar to the compound 21 but has an lower panel fragment corresponding to that in the compound 18b, according to the reaction schemes represented by the chemical equations (2-6) to (2-8).

Evaluation of the Series of the Quinoxaline-Fused Dibenzosuberane Based Helicenes as Materials for the Organic Electroluminescent Device The compounds of the chemical formulas (1) to (4), synthesized through the protocols provided as Example 1 to Example 7a, 7b, 7c, and Example 8 to Example 15, respectively, were evaluated for their thermal, photophysical, and electrochemical properties, such as their wavelengths of maximum absorption (Abs. $\lambda_{max}$), wavelengths of maximum emission (Em, $\lambda_{max}$), full width at half maximum (FWHM), quantum yield ($\Phi_f$), oxidation potential ($E_{ox}$), reduction potential ($E_{red}$), the highest occupied molecular orbital ($E_{HOMO}$), the lowest occupied molecular orbital ($E_{LUMO}$), energy gap ($E_g$), the melting temperature ($T_m$), the glass transition temperature ($T_g$) and the decomposition temperature ($T_d$).

The wavelengths of maximum absorption (Abs. $\lambda_{max}$), the wavelengths of maximum emission (Em, $\lambda_{max}$), and full width at half maximum (FWHM) were measured in a solution using dichloromethane (for the compounds of the chemical formulas (1), (3) and (4)) or toluene (for the chemical formula (2)) as the solvent. Quantum yield ($\Phi_f$) was measured with Hamamatsu C9920. The melting temperature and the glass transition temperature were measured by a differential scanning calorimeter (DSC). The decomposition temperatures were measured by a thermogravimetric analyzer (TGA) and are considered to be the basis of the thermal stability for the device fabrication and optoelectronic performance.

The electrochemical properties, including $E_{ox}$, $E_{red}$, $E_{HOMO}$, $E_{LUMO}$, and $E_g$, were measured by way of cyclic voltammetry (CV) in a solution using dichloromethane as a solvent. The energy levels of HOMO ($E_{HOMO}$), energy levels of LUMO ($E_{LUMO}$) and the relative energy gaps of the compounds were determined by analyzing the corresponding UV-VIS absorption spectra. Platinum wire electrode was used as the counter (auxiliary) electrode, carbon electrode was used as the working electrode and Ag was used as the reference electrode (which was immersed in hydrochloric acid in advance before use). Ferrocene was used as a standard. The redox potential of the ferrocene/ferrocenium (Fe/Fe+) redox couple was assumed at 0.51 V relative to vacuum. The CV curves were calibrated using the Fe/Fe$^+$ redox couple as an external standard which was measured under same condition before and after the measurement of samples. The energy level of Fe/Fe+ was assumed at −4.8 eV to vacuum. The energy gap ($E_g$) was the difference between the HOMO energy level ($E_{HOMO}$) and the energy level of LUMO ($E_{LUMO}$).

Those properties of the compounds of the chemical formula (1) to chemical formula (4) are shown in Table 1.

TABLE 1

| compound | chemical formula (1) | chemical formula (2) | chemical formula (3) | chemical formula (4) |
|---|---|---|---|---|
| Abs · $\lambda_{max}$(nm) | 284, 369 | 322, 478 | 315, 450 | 285, 364 |
| Em, $\lambda_{max}$(nm) | 500 | 652 | 586 | 498 |
| FWHM(nm) | 88 | 113 | 100 | 85 |

TABLE 1-continued

| compound | chemical formula (1) | chemical formula (2) | chemical formula (3) | chemical formula (4) |
|---|---|---|---|---|
| $\Phi_f$ (%) | 58 | 24 | 64 | 64 |
| $E_{OX}$ (V) | — | 0.61, 0.82 | 1.00 | — |
| $E_{red}$ (V) | −1.60 | −1.64 | −1.60 | −1.66 |
| $E_{HOMO}$ (eV) | −5.98 | −5.28 | −5.69 | −5.92 |
| $E_{LUMO}$ (eV) | −3.20 | −3.16 | −3.20 | −3.14 |
| $E_g$ (eV) | 2.78 | 2.12 | 2.49 | 2.78 |
| $T_m$ (° C.) | 289 | 292 | 466 | 400 |
| $T_g$ (° C.) | 127 | 108 | 146 | 137 |
| $T_d$ (° C.) | 398 | 385 | 547 | 507 |

The absorption spectra of the compounds of the chemical formula (1) and chemical formula (4) were very similar because both of the compounds have the same structures at the upper panel fragments. In addition, the maximal emission peaks of the compounds of chemical formula (1) and chemical formula (4) appeared around 500 nm and 498 nm, respectively. Thus, they emitted bluish green lights. The quinoxaline-fused fragments of the compounds of the chemical formula (1) and chemical formula (4) were excellent electron acceptors and high conjugation systems. In addition, at $C_1$ and $C_4$ positions, these quinoxaline-fused fragments were conjugated with p-methoxyphenyl groups which are strong electron donors. Such configuration may donate the electrons to the core template of the quinoxaline-fused fragments. Thus, these two compounds have high fluorescent quantum yields.

The compounds of the chemical formula (2) and chemical formula (3) have arylamine substituents at $C_1$ and $C_4$ positions, whereas the compound of the chemical formula (2) has p-phenyl-diphenyl amino groups and chemical formula (3) has N-methyl-phenyl-amino groups. Such configurations of the compounds of the chemical formulas (2) and (3) may further increase the extent of conjugation of the quinoxaline-fused fragments when compared with the compounds of the chemical formulas (1) and (4). According to Table 1, the peaks of maximum absorption of the compounds of the chemical formula (2) and chemical formula (3) appeared around 450 nm and 478 nm, respectively, which correspond to the intramolecular charge transfer of the lone pair electrons from the nitrogen of the arylamine groups to the core template of the quinoxaline-fused fragment (n-π* transitions). The peak of maximum emission of the compound of the chemical formula (2) appeared around 652 nm, with a full width at half maximum of 113 nm, which was in the range of pure red light (640 nm). In addition, the quantum yield of the compound of the chemical formula (2) was as high as 24%, which represented that the compound of the chemical formula (2) was suitable as an excellent red electroluminescent material. The peak of maximum emission of the compound of the chemical formula (3) appeared around 586 nm, with a full width at half maximum of 100 nm, and this compound emitted a yellow-orange light in the solution. In addition, the quantum yield of the compound of the chemical formula (3) was as high as 64%, which represents that the compound of the chemical formula (3) was suitable as an excellent yellow-orange electroluminescent material.

According to Table 1, the glass transition temperatures ($T_g$) of these four compounds ranged from 105° C. to 146° C. These compounds have excellent thermal stability as organic electroluminescent materials. The compound of chemical formula (3) with the highest molecular weight among these four compounds, has the highest melting temperature (466° C.) and glass transition temperature (146° C.). The decomposition temperatures of the compounds of chemical formula (1) to chemical formula (4) were all higher than 350° C., so that the decomposition caused by the heat is not easily occurred during the thermal vacuum deposition process. Moreover, the decomposition temperatures of the compounds of chemical formula (3) and chemical formula (4) were even higher (507° C. to 547° C.), which may be attributable to the higher molecular weight of the compound of the chemical formula (3) and the greater sterically-hindered structure of its lower panel of the compound of the chemical formula (4), respectively. Based on the reasons mentioned above, these four compounds have excellent thermal stabilities, and are quite beneficial for the organic electroluminescent device application.

The reduction potentials of the compounds of the chemical formula (1) to chemical formula (4) are occurred at their quinoxaline-fused fragments and are ranged from −1.60 V to −1.66 V. The compound of the chemical formula (2) has two sets of reversible oxidation potentials, which is attributed to the two arylamine groups at its upper panel. The compound of the chemical formula (3) has only one set of reversible oxidation potential, which is attributed to the two sets of triarylamine groups at its upper panel. The reversible oxidation potential (1.00 V) of the compound of the chemical formula (3) was highest among these four compounds, which is attributed to the good conjugation between its core quinoxaline-fused fragment and the two sets of triarylamine groups at both sides. The oxidation or reduction profiles of the compounds of the chemical formula (1) to chemical formula (4) in CVs are all reversible, which are quite beneficial to the transport of electrons and holes. Therefore, these compounds are suitable for the organic electroluminescent device with good stability and luminous efficiency.

The $E_{HOMO}$ of the compounds of the chemical formula (1) and chemical formula (4) are ranged from −5.98 eV to −5.28 eV. The $E_{LOMO}$ of the compounds of the chemical formula (1) and chemical formula (4) are ranged from −3.20 eV to −3.12 eV. Comparing to the conventional metal cathode materials (i.e., LiF/Al) and ITO anode, the energy gaps between the $E_{LOMO}$ of the compounds of the chemical formula (1) and the chemical formula (4) to that of the metal cathode are about 0.50 eV to 0.56 eV, and the energy gap between the $E_{HOMO}$ of the compounds of the chemical formula (1) and chemical formula (4) to that of ITO anode are about 1.22 eV to 1.28 eV. Moreover, the compounds of the chemical formula (1) and chemical formula (4) have a core template with a quinoxaline-fused fragment and have the substituents which are mostly simple aromatic ring derivatives. Hence, the compounds of the chemical formula (1) and chemical formula (4) not only can be light-emitting materials but also theoretically have electron transport properties. On the other hand, the arylamine substituents of the compounds of the chemical formula (2) and chemical formula (3) have hole transport properties, and their core quinoxaline-fused fragments have electron transport properties, which will result in that the compounds of the chemical formula (2) and chemical formula (3) have ambipolar properties and are suitable not only to be materials for the layer with both electron transport and light-emitting properties but also to be materials for the layer with both hole transport and light-emitting properties of the organic electroluminescent device.

The Device Efficiency for Compounds (Chemical Formula (1) to Chemical Formula (4)) which were Used in the Organic Electroluminescent Devices Configurations of the Organic Electroluminescent Devices The unit structure of the present Example is ITO/hole transport layer (40 nm)/materials for testing (40 nm)/hole blocking layer (10 nm)/electron transport layer (40 nm)/electron injection layer (1 nm)/Al. In the units 2, 5, 9, and 10, the to-be-tested materials of the chemical formula (1) to chemical formula (4) are used for the layer with both electron transport and light-emitting properties. In the units 7 and 8, the to-be-tested materials of the chemical formula (2) and chemical formula (3) are used for the layer with both hole transport and light-emitting properties. In the units 4, 6 and 11, the to-be-tested materials of the chemical formula (1), chemical formula (3) and chemical formula (4) are used for the light-emitting layer. The material of first electrode layer is ITO. The material of second electrode layer is aluminum with the thickness of 100 nm. The material of the hole transport layer is N,N'-Di(1-naphthyl)-N,N'-diphenyl-(1,1'-biphenyl)-4,4'-diamine (NPB) with the thickness of 40 nm. The material of hole blocking layer is 2,9-dimethyl-4,7-diphenyl-1,10-phenanthroline (BCP) with the thickness of 10 nm. The material of the electron transport layer is tris-(8-hydroxyquinoline) aluminum ($Alq_3$) with the thickness of 40 nm. The material of the electron injection layer is LiF with the thickness of 1 nm.

Efficiency Evaluation of the Organic Luminescent Units Fabricated as Above

The organic luminescent units fabricated as above were evaluated for their wavelengths of maximum emission (Em, $\lambda_{max}$), turn-on voltages ($V_{on}$), working voltages ($V_{@20\ mA/cm^2}$) at 20 $mA/cm^2$, current efficiencies $\eta_c$ (cd/A), power efficiencies $\eta_p$ (lm/W), external quantum efficiencies $\eta_{ext}$ (EQE, %), and luminance (L, $cd/m^2$). The device configurations of each OLED unit are shown in Table 2 and the characteristics of these OLED units are shown in Table 3.

TABLE 2

| Unit | Second electrode | Electron injection | Electron transport | Hole blocking | To-be-tested material | Hole transport | First electrode |
|---|---|---|---|---|---|---|---|
| 1 | Al | LiF | Alq₃ | — | — | NPB | ITO |
| 2 | Al | LiF | — | — | Chemical formula (1) | NPB | ITO |
| 3 | Al | LiF | Alq₃ | BCP | — | NPB | ITO |
| 4 | Al | LiF | Alq₃ | BCP | Chemical formula (1) | NPB | ITO |

TABLE 2-continued

| Unit | Second electrode | Electron injection | Electron transport | Hole blocking | To-be-tested material | Hole transport | First electrode |
|---|---|---|---|---|---|---|---|
| 5 | Al | LiF | — | — | Chemical formula (4) | NPB | ITO |
| 6 | Al | LiF | Alq₃ | BCP | Chemical formula (4) | NPB | ITO |
| 7 | Al | LiF | Alq₃ | BCP | Chemical formula (2) | — | ITO |
| 8 | Al | LiF | Alq₃ | BCP | Chemical formula (3) | — | ITO |
| 9 | Al | LiF | — | — | Chemical formula (2) | NPB | ITO |
| 10 | Al | LiF | — | — | Chemical formula (3) | NPB | ITO |
| 11 | Al | LiF | Alq₃ | BCP | Chemical formula (3) | NPB | ITO |

TABLE 3

| | Unit | | | | | | | | | | |
|---|---|---|---|---|---|---|---|---|---|---|---|
| | 1 | 2 | 3 | 4 | 5 | 6 | 7 | 8 | 9 | 10 | 11 |
| Em, $\lambda_{max}$ | 522 | 514 | 514 | 516 | 544 | 544 | 650 | 578 | 656 | 584 | 588 |
| fwhm | 112 | 112 | 100 | 98 | 114 | 112 | 128 | 118 | 124 | 116 | 114 |
| $V_{on}$ (V) | 4.7 | 4.2 | 4.2 | 6 | 4.4 | 6.2 | 4.5 | 5.1 | 4.8 | 2.8 | 5 |
| $V_{@20mA/cm^2}$ | 6.6 | 7.6 | 7.6 | 10.4 | 11.1 | 11.3 | 7.53 | 7.72 | 8.14 | 7.21 | 8.04 |
| $\eta_{ext}$ (%) | 1.36 | 0.41 | 0.41 | 2.3 | 0.32 | 1 | 0.24 | 0.20 | 0.4 | 0.34 | 1.42 |
| $\eta_c$ (cd/A) | 4.2 | 1.3 | 1.3 | 7.2 | 1.1 | 3.2 | 0.2 | 0.3 | 0.3 | 1.0 | 3.8 |
| $\eta_p$ (lm/W) | 2 | 0.6 | 0.6 | 2.2 | 0.3 | 0.9 | 0.1 | 0.1 | 0.1 | 0.4 | 1.4 |
| L | 838 | 262 | 262 | 1427 | 217 | 631 | 30 | 57 | 48 | 172 | 690 |

Regarding to the units 1 to 4, the to-be-tested materials were the compound of the chemical formula (1) and emitted green fluorescents. In the unit 2, the compound of the chemical formula (1) was used as the material of the layer having both electron transport and light-emitting properties, and at 20 $mA/cm^2$ its $\eta_{ext}$ was 0.4%, $\eta_c$ was 1.3 cd/A, $\eta_p$ was 0.6 lm/W and luminance was 262 $cd/m^2$. On the other hand, in the unit 4, the compound of the chemical formula (1) was used as the material of the light-emitting layer, and at 20 $mA/cm^2$ its $\eta_{ext}$ was 2.3%, $\eta_c$ was 7.2 cd/A, $\eta_p$ was 2.2 lm/W, and luminance was 1427 $cd/m^2$. Accordingly, the units 2 and 4 are both suitable to be green organic luminescent units, and, in general, the unit 4 may have a better performance than the unit 2. Regarding to the units 5 to 6, the to-be-tested materials were the compound of the chemical formula (4) and emitted yellow-green fluorescents. In the unit 5, the compound of the chemical formula (4) was used as the material of the layer having both electron transport and light-emitting properties, and at 20 $mA/cm^2$ its $\eta_{ext}$ was 0.3%, $\eta_c$ was 1.1 cd/A, $\eta_p$ was 0.3 lm/W and luminance was 217 $cd/m^2$. On the other hand, in the unit 6, the compound of the chemical formula (4) was as the material of the light-emitting layer, and at 20 $mA/cm^2$ its $\eta_{ext}$ was 1.0%, $\eta_c$ was 3.2 cd/A, $\eta_p$ was 0.9 lm/W, and luminance was 630 cd/m². Accordingly, the units 5 and 6 are suitable to be yellow-green organic luminescent units, and, in general, the unit 6 may have a better performance than the unit 5. Therefore, in the present Example, the units which have the helicenes of the chemical formula (1) and chemical formula (4) functioned as pure light-emitting layer had better performance in general.

As mentioned above, the compounds of the chemical formula (2) and chemical formula (3) have ambipolar properties including hole transport and electron transport. Thus, in the units 7 and 8 in the present Example, the compounds of the chemical formula (2) (for unit 7) and chemical formula (3) (for unit 8) were used as the materials of the layer having both hole transport and light-emitting properties. According to Table 3, the BCP hole blocking layer effectively restrained the holes to stay in the light-emitting layer. The $CIE_{xy}$ coordinates of the unit 7 was (0.65, 0.34), which represented it emitted a saturated red light. At 20 mA/cm², the unit 7 had an $\eta_{ext}$ of 0.3%, $\eta_c$ of 0.2 cd/A, and $\eta_p$ of 0.1 lm/W. Meanwhile, the unit 8 emitted an orange light, and, at 20 mA/cm², it had an $\eta_{ext}$ of 0.2%, $\eta_c$ of 0.2 cd/A, and $\eta_p$ of 0.1 lm/W. In addition, the energy gaps between the $E_{HOMO}$ of the compounds of the chemical formula (2) and the chemical formula (3) and that of $Alq_3$ are 0.72 eV (chemical formula (2)) and 0.31 eV (chemical formula (3)), respectively, some holes in the units were found to still enter $Alq_3$ without the BCP hole blocking layer. Such phenomena might be attributable to that the upper panel of the compounds of the chemical formula (2) and chemical formula (3) which have two para-linked arylamine substituents to the aromatic ring of the fused quinoxaline fragment, which is similar to the configuration of the hole transport material NPB. Therefore, such configurations of the compounds of the chemical formula (2) and chemical formula (3) may help the holes to be transported to the $Alq_3$ electron transport layer much easier.

The efficacies of the units 9 and 10 were evaluated, and the compounds of the chemical formula (2) and chemical formula (3) were used as the materials of the layer having both electron transport and light-emitting properties, and NPB was used as the material of the hole transport layer. The $CIE_Y$ coordinates of the unit 9 was (0.66, 0.33), which represented it emitted an ordinary saturated red luminescence. At 20 mA/cm², the unit 9 had an $\eta_{ext}$ of 0.4%, $\eta_c$ of 0.3 cd/A, and $\eta_p$ of 0.1 lm/W. Meanwhile, the unit 10 emitted an orange luminescence, and, at 20 mA/cm², it had an $\eta_{ext}$ of 0.34%, $\eta_c$ of 1.0 cd/A, and $\eta_p$ of 0.4 lm/W.

In addition, in the unit 11, the compound of the chemical formula (3) was used as the material of the light-emitting layer. The unit 11 was found to emit an orange luminescence, and, at 20 mA/cm², the unit 11 had an $\eta_{ext}$ of 1.42%, $\eta_c$ of 3.8 cd/A, and $\eta_p$ of 1.4 lm/W. Accordingly, the unit 11 was suitable for an organic luminescent units which emitted an orange luminescence.

In summary, a series of materials for organic electroluminescent device which emitted green/yellow-green/orange/yellow-orange/red luminescence are provided according to the present disclosure. The quinoxaline-fused dibenzosuberane based helicenes according to the embodiments of the present invention have excellent fluorescence quantum effects and thermal stabilities. Therefore, the quinoxaline-fused dibenzosuberane based helicenes are suitable for organic electroluminescent devices. Meanwhile, suitable configurations of units can also be found in the embodiments, which have good stabilities and luminous efficiencies.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:
1. An organic electroluminescent device, comprising:
a first electrode layer;
a second electrode layer; and
an organic luminescent unit, deposited between the first electrode layer and the second electrode layer, wherein the organic luminescent unit has at least a quinoxaline-fused dibenzosuberane based helicene as shown in General Formula (1),

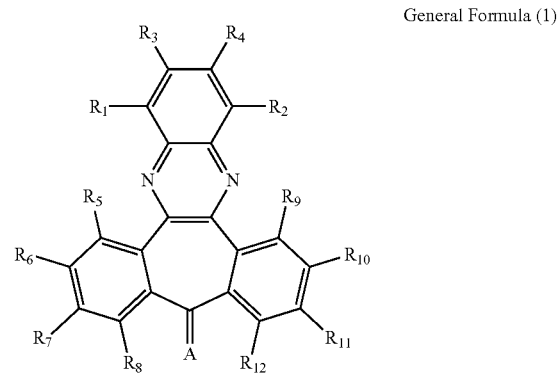

General Formula (1)

wherein A is represented by General Formula (2), General Formula (3a) or General Formula (3b);

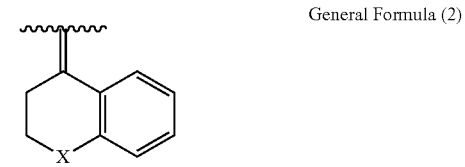

General Formula (2)

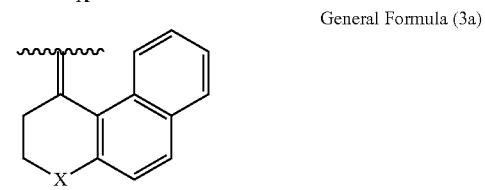

General Formula (3a)

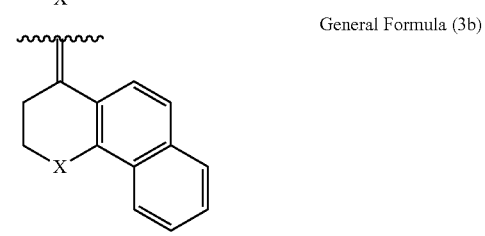

General Formula (3b)

wherein X is an oxygen atom, sulfur atom, amino group, or $-(CH_2)_n-$, n is 0, 1, or 2; $R_1$ and $R_2$ are both independently a hydrogen atom, a halogen atom, General Formula (4), General Formula (5) or General Formula (6); and General Formula (4)

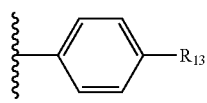

General Formula (5)

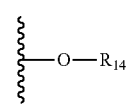

General Formula (6)

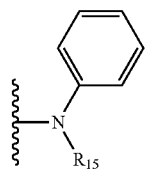

wherein $R_3$ to $R_{15}$ are independently selected from the group consisting of a hydrogen atom, a halogen atom, a cyano group, an alkyl group, a cycloalkyl group, an alkoxy group, a haloalkyl group, a thioalkyl group, a silyl group, an alkenyl group, an aryl group, and an amino group.

2. The organic electroluminescent device of claim 1, wherein the alkyl group is selected from the group consisting of a substituted or unsubstituted straight-chain alkyl group with the carbon number of 1 to 6, and a substituted or unsubstituted branched-chain alkyl group with the carbon number of 3 to 6, the cycloalkyl group is a substituted or unsubstituted cycloalkyl group with the carbon number of 3 to 6, the alkoxy group is selected from the group consisting of a substituted or unsubstituted straight-chain alkoxy group with the carbon number of 1 to 6, and a substituted or unsubstituted branched-chain alkoxy group with the carbon number of 3 to 6, the haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6, the thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6, the silyl group is selected from the group consisting of a substituted or unsubstituted straight-chain silyl group with the carbon number of 1 to 6, and a substituted or unsubstituted branched-chain silyl group with the carbon number of 3 to 6, the alkenyl group is selected from the group consisting of a substituted or unsubstituted straight-chain alkenyl group with the carbon number of 2 to 6, and a substituted or unsubstituted branched-chain alkenyl group with the carbon number of 3 to 6, the aryl group is a substituted or unsubstituted aromatic hydrocarbon with the carbon number of 6 to 16, or a substituted or unsubstituted hetero aromatic ring with the carbon number of 5 to 16, the amino group is secondary amino group or tertiary amino group.

3. The organic electroluminescent device of claim 1, wherein $R_{13}$ is a substituted or unsubstituted straight-chain alkyl group with the carbon number of 1 to 6 or an amino group.

4. The organic electroluminescent device of claim 1, wherein $R_{14}$ is a substituted or unsubstituted straight-chain alkyl group with the carbon number of 1 to 6.

5. The organic electroluminescent device of claim 1, wherein $R_{15}$ is an aryl group or a substituted or unsubstituted straight-chain alkyl group with the carbon number of 1 to 6.

6. The organic electroluminescent device of claim 1, wherein the quinoxaline-fused dibenzosuberane based helicene has a structure represented by one of following chemical formula I to chemical formula IV chemical formula I

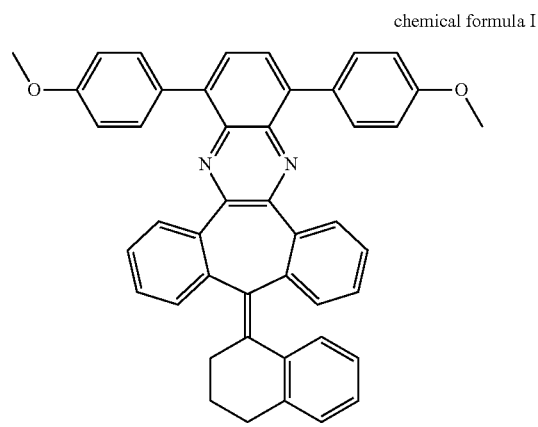

chemical formula II

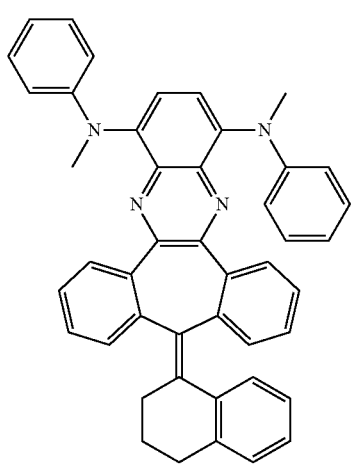

chemical formula III

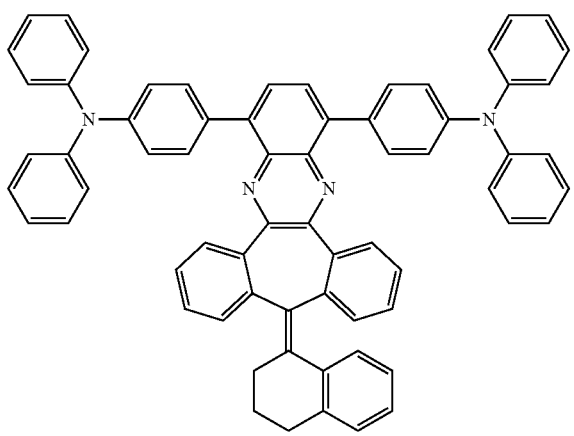

-continued

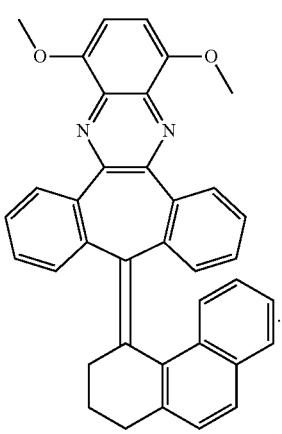

chemical formula IV

7. The organic electroluminescent device of claim 1, wherein the organic luminescent unit comprises an organic luminescent layer.

8. The organic electroluminescent device of claim 7, wherein the organic luminescent unit further comprises a hole transport layer and an electron transport layer, and the organic luminescent layer is deposited between the hole transport layer and the electron transport layer.

9. The organic electroluminescent device of claim 7, wherein the organic luminescent unit further comprises a hole injection layer, a hole transport layer, an electron transport layer and an electron injection layer, and the hole transport layer, the organic luminescent layer and the electron transport layer are sequentially deposited between the hole injection layer and the electron injection layer.

10. The organic electroluminescent device of claim 7, wherein the organic luminescent layer comprises the quinoxaline-fused dibenzosuberane based helicene.

\* \* \* \* \*